(12) United States Patent
McDaniel et al.

(10) Patent No.: US 12,085,443 B2
(45) Date of Patent: Sep. 10, 2024

(54) FIBER-COUPLED BROADBAND LIGHT SOURCE

(71) Applicant: UbiQD, Inc., Los Alamos, NM (US)

(72) Inventors: Hunter McDaniel, Los Alamos, NM (US); Nikolay S. Makarov, Los Alamos, NM (US); Matthew R. Bergren, Los Alamos, NM (US)

(73) Assignee: UbiQD, Inc., Los Alamos, NM (US)

( * ) Notice: Subject to any disclaimer, the term of this patent is extended or adjusted under 35 U.S.C. 154(b) by 31 days.

(21) Appl. No.: 17/746,911

(22) Filed: May 17, 2022

(65) Prior Publication Data

US 2022/0276091 A1 Sep. 1, 2022

Related U.S. Application Data

(62) Division of application No. 16/009,158, filed on Jun. 14, 2018, now abandoned.

(60) Provisional application No. 62/519,857, filed on Jun. 14, 2017.

(51) Int. Cl.
| | |
|---|---|
| *G01J 3/02* | (2006.01) |
| *A61B 5/00* | (2006.01) |
| *F21V 8/00* | (2006.01) |
| *G01J 3/10* | (2006.01) |
| *G01J 3/42* | (2006.01) |
| *G02B 6/42* | (2006.01) |

(52) U.S. Cl.
CPC .......... *G01J 3/0218* (2013.01); *A61B 5/0075* (2013.01); *G01J 3/108* (2013.01); *G01J 3/42* (2013.01); *G02B 6/0003* (2013.01); *A61B 2562/0233* (2013.01); *G01J 3/10* (2013.01); *G02B 6/0008* (2013.01); *G02B 6/4296* (2013.01)

(58) Field of Classification Search
CPC .. G01J 3/0218; G01J 3/108; G01J 3/42; G01J 3/10; A61B 5/0075; A61B 2562/0233; G02B 6/0003; G02B 6/0008; G02B 6/4296
See application file for complete search history.

(56) References Cited

U.S. PATENT DOCUMENTS

| | | | |
|---|---|---|---|
| 5,546,493 A * | 8/1996 | Noguchi | C07F 9/067 385/125 |
| 6,103,535 A | 8/2000 | Pilevar et al. | |
| 6,337,945 B1 * | 1/2002 | Kingstone | G02B 6/0008 385/116 |

(Continued)

FOREIGN PATENT DOCUMENTS

WO 2018209000 A1 11/2018

OTHER PUBLICATIONS

Schneebeli et al.; Integrated liquid-core optical fibers for ultra-efficient nonlinear liquid photonics; published in 2012; Optical Express; vol. 20 Issue 7; pp. 8148-8154 (Year: 2012).*

(Continued)

*Primary Examiner* — Chao Sheng
(74) *Attorney, Agent, or Firm* — John A. Fortkort; Fortkort & Houston PC

(57) ABSTRACT

An optical element is provided which includes an optical fiber, and a plurality of fluorophores disposed inside the optical fiber. The fluorophores have a quantum yield greater than 50%, and emit a spectrum of light having a maximum intensity at wavelengths within the range of 400 nm to 2000 nm.

18 Claims, 14 Drawing Sheets

(56) References Cited

U.S. PATENT DOCUMENTS

| | | | |
|---|---|---|---|
| 6,514,277 B1 | 2/2003 | Lilge et al. | |
| 9,382,432 B1 | 7/2016 | McDaniel | |
| 9,540,523 B1 | 1/2017 | McDaniel | |
| 9,964,488 B2 | 5/2018 | McDaniel | |
| 10,082,387 B2 | 9/2018 | Bergren et al. | |
| 10,170,022 B2 | 1/2019 | McDaniel | |
| 2002/0186921 A1* | 12/2002 | Schumacher | G02B 6/0008 |
| | | | 385/128 |
| 2010/0041158 A1 | 2/2010 | Basu et al. | |
| 2012/0009683 A1* | 1/2012 | Gee | C09B 11/08 |
| | | | 546/100 |
| 2014/0030193 A1 | 1/2014 | Searson et al. | |
| 2016/0230213 A1* | 8/2016 | Ying | C12Q 1/686 |

OTHER PUBLICATIONS

K. Kieu, L. Schneebeli, R. A. Norwood, and N. Peyghambarian, Integrated liquid-core optical fibers for ultraefficient nonlinear liquid photonics, Optics Express, vol. 20, No. 7, 8148 (Mar. 26, 2012).

Rami Nachabé, Benno H. W. Hendriks, Marjolein van der Voort, Adrien E. Desjardins, and Henricus J. C. M. Sterenborg, Estimation of biological chromophores using diffuse optical spectroscopy: benefit of extending the UV-VIS wavelength range to include 1000 to 1600 nm, Biomedical Optics Express vol. 1, Issue 5, pp. 1432-1442 (2010).

* cited by examiner

FIBER-COUPLED BROADBAND LIGHT SOURCE

CROSS-REFERENCE TO RELATED APPLICATIONS

This application is a divisional of U.S. Ser. No. 16/009,158, filed Jun. 14, 2018, having the same inventors, and the same title, and which is incorporated herein in its entirety; which claims the benefit of priority from U.S. Provisional Application No. 62/519,857 filed Jun. 14, 2017, having the same inventors, and the same title, and which is incorporated herein in its entirety.

FIELD OF THE DISCLOSURE

The present disclosure relates generally to down-conversion materials and devices, and more specifically to fluorescent material-coupled fiber optic elements for medical diagnostics.

BACKGROUND OF THE DISCLOSURE

Minimally-invasive image-guided procedures are highly important for safe clinical practice. Current standard of care requires expensive image guided techniques that could benefit from real-time feedback at the instrument tip. The end users (surgeons/patient) will benefit greatly from advancements in Spectral Tissue Sensing (STS) in their effort to reduce false negatives and improve the outcome of oncology diagnosis and treatment. To reach commercial viability and make STS systems widely available, the cost and size of these photonic needle systems must be reduced dramatically while also improving the underlying optical source.

According to the American Cancer Society, in 2017 alone, there will be an estimated 1,688,780 new cancer cases diagnosed and 600,920 cancer deaths in the US. The United States has the highest economic loss from cancer in absolute dollars, and the disease costs the country 1.73% of its GDP. Diagnosis of cancer at its earliest, most treatable stage gives patients the greatest chance for survival. Furthermore, accurate treatment reduces risks of recurrence and metastasis.

STS is widely used as a tool for determining the optical properties of tissues. Such tools are being investigated as an aid for detecting cancers, monitoring changes in tissue optical properties that reflect morphological and physiological changes, and monitoring therapy response (for instance, in photodynamic therapy). Wavelengths up to 1600 nm are actively used to determine concentrations of water and lipid, which have distinct absorption peaks in the near-infrared (NIR) spectral region. Multiple clinical studies have shown that STS can provide information on intrinsic physiological tissue properties, such as oxy- and deoxy-hemoglobin, content of water, and lipids, which can be successfully used to diagnose breast cancer with sensitivity and specificity as high as 100% and 96% respectively. For instance, tissue optical index (compound function of deoxy-hemoglobin, water and lipid tissue concentration) describes tissue metabolism, structure and cellularity, and thus can be directly used to distinguish between healthy and cancer tissues. So far, however, it has been very difficult to realize a low-cost miniature system, due in part to inadequate illumination sources.

SUMMARY OF THE DISCLOSURE

Figure 1:
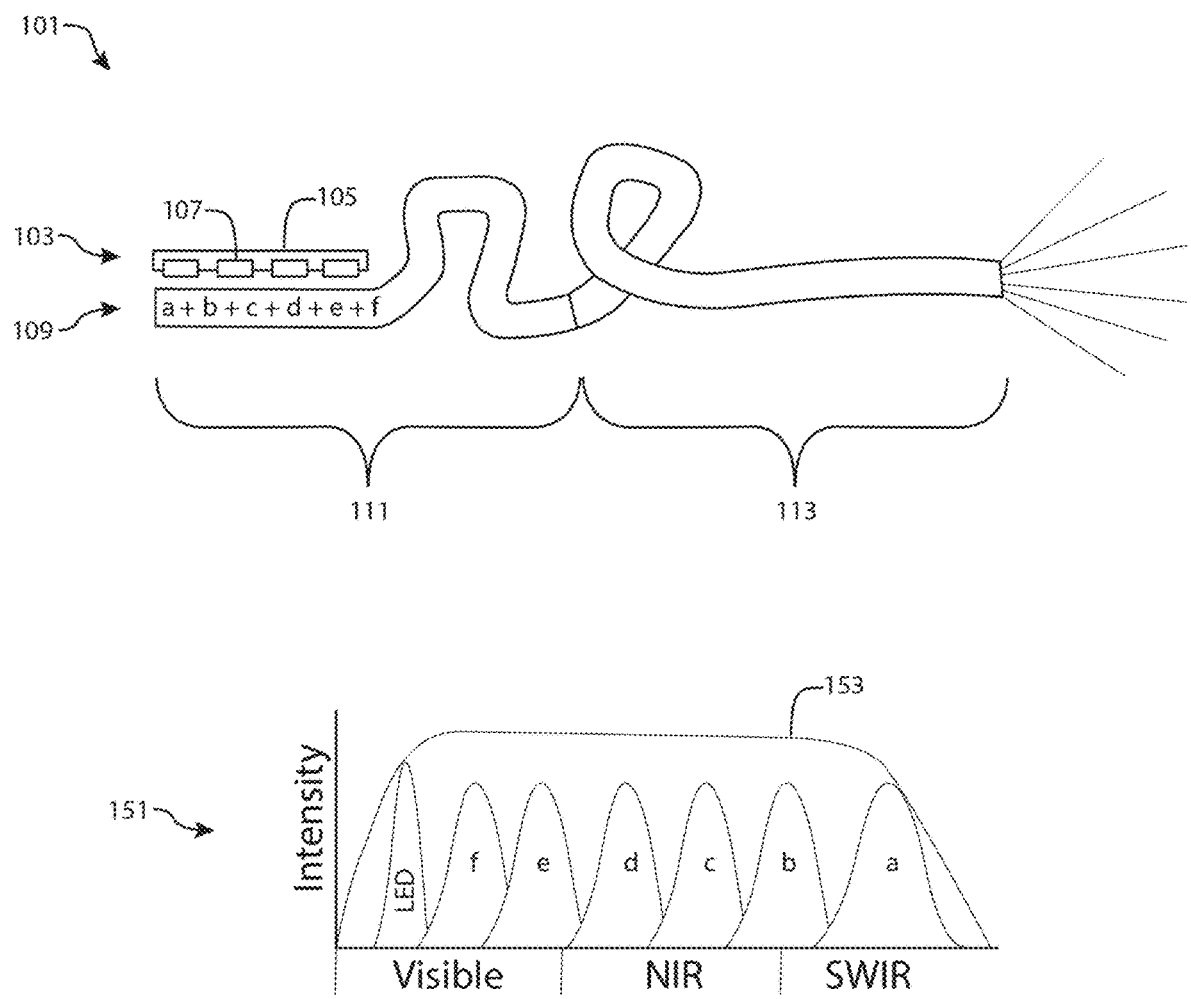
FIG. 1 is a schematic that depicts one mode of the invention wherein a blue light excites along a fluorophore-integrated fiber containing a mixture of fluorophores. This mode is a simple approach.

In one aspect, an optical element is provided which comprises an optical fiber; and a plurality of fluorophores disposed inside said optical fiber; wherein said fluorophores have a quantum yield greater than 50%, wherein said fluorophores emit a spectrum of light having a maximum intensity at wavelengths within the range of 400 nm to 2000 nm.

In another aspect, a method is provided for performing a spectral tissue sensing (STS) analysis on a subject. The method comprises (a) providing an instrument which includes an input source of electromagnetic radiation and an optical element, wherein the optical element comprises an optical fiber and a plurality of fluorophores disposed inside said optical fiber, wherein said fluorophores have a quantum yield greater than 50%, wherein said fluorophores emit a spectrum of light having a maximum intensity at wavelengths within the range of 400 nm to 2000 nm, and wherein said fluorophores emit a spectrum of light having full-width at half maximum intensity of greater than 40 nm; (b) generating an output source of electromagnetic radiation by directing electromagnetic radiation from the input source along an optical path that includes the optical element; (c) irradiating a portion of tissue with electromagnetic radiation from the output source; and (d) performing STS analysis on the irradiated tissue.

DETAILED DESCRIPTION

1. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly indicates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure relates. Suitable methods and compositions are described herein for the practice or testing of the compositions, systems and methodologies described herein. However, it is to be understood that other methods and materials similar or equivalent to those described herein may be used in the practice or testing of these compositions, systems and methodologies. Consequently, the compositions, materials, methods, and examples disclosed herein are illustrative only, and are not intended to be limiting. Other features of the disclosure will be apparent to those skilled in the art from the following detailed description and the appended claims.

Unless otherwise indicated, all numbers expressing quantities of components, percentages, temperatures, times, and so forth, as used in the specification or claims are to be understood as being modified by the term "about." Unless otherwise indicated, non-numerical properties such as colloidal, continuous, crystalline, and so forth as used in the specification or claims are to be understood as being modified by the term "substantially," meaning to a great extent or degree. Accordingly, unless otherwise indicated implicitly or explicitly, the numerical parameters and/or non-numerical properties set forth are approximations that may depend on the desired properties sought, the limits of detection under standard test conditions or methods, the limitations of the processing methods, and/or the nature of the parameter or property. When directly and explicitly distinguishing embodiments from discussed prior art, the embodiment numbers are not approximations unless the word "about" is recited.

Carcinogen: A material that has been shown to directly or indirectly cause cancer in any mammal.

Fiber Optic: A cylindrical shaped waveguide for light. The light to be guided can be UV, visible, NIR, or IR. The fiber can be made of a polymer or ceramic. Typical fiber optic materials are glass, acrylic polymers, vinyls, ionoplast, and silicones.

Photoluminescence (PL): The emission of light (electromagnetic radiation, photons) after the absorption of light. It is one form of luminescence (light emission) and is initiated by photoexcitation (excitation by photons).

Toxic: Denotes a material that can damage living organisms due to the presence of phosphorus or heavy metals such as cadmium, lead, or mercury.

Quantum Dot (QD): A nanoscale particle that exhibits size-dependent electronic and optical properties due to quantum confinement. The quantum dots disclosed herein preferably have at least one dimension less than about 50 nanometers. The disclosed quantum dots may be colloidal quantum dots, i.e., quantum dots that may remain in suspension when dispersed in a liquid medium. Some of the quantum dots which may be utilized in the compositions, systems and methodologies described herein are made from a binary semiconductor material having a formula MX, where M is a metal and X typically is selected from sulfur, selenium, tellurium, nitrogen, phosphorus, arsenic, antimony or mixtures thereof. Exemplary binary quantum dots which may be utilized in the compositions, systems and methodologies described herein include CdS, CdSe, CdTe, PbS, Pb Se, PbTe, ZnS, ZnSe, ZnTe, InP, InAs, $Cu_2S$, and $In_2S_3$. Other quantum dots which may be utilized in the compositions, systems and methodologies described herein are ternary, quaternary, and/or alloyed quantum dots including, but not limited to, ZnSSe, ZnSeTe, ZnSTe, CdSSe, CdSeTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, $CuInS_2$, $CuInSe_2$, $CuInGaSe_2$, $CuInZnS_2$, $CuZnSnSe_2$, $CuIn(Se,S)_2$, $CuInZn(Se,S)_2$, and $AgIn(Se,S)_2$ quantum dots, although the use of non-toxic quantum dots is preferred. Embodiments of the disclosed quantum dots may be of a single material, or may comprise an inner core and an outer shell (e.g., a thin outer shell/layer formed by any suitable method, such as cation exchange). The quantum dots may further include a plurality of ligands bound to the quantum dot surface.

Quantum Yield (QY): The ratio of the number of emitted photons to the number of absorbed photons for a fluorophore.

Fluorophore: a material which absorbs a first spectrum of light and emits a second spectrum of light.

Stokes shift: the difference in energy between the positions of the absorption shoulder or local absorption maximum and the maximum of the emission spectrum.

Emission spectrum: Those portions of the electromagnetic spectrum over which a photoluminescent material exhibits photoluminescence (in response to excitation by a light source) whose amplitude is at least 1% of the peak PL emission.

Luminescent concentrator (LC): A device for converting a spectrum and photon flux of electromagnetic radiation into a new narrower spectrum with a higher photon flux. LCs operate on the principle of collecting radiation over a large area by absorption, converting it to a new spectrum by PL, and then directing the generated radiation into a relatively small output target by total internal reflection.

Luminescent solar concentrator (LSC): used here as a synonym of LC.

Photon flux: The number of photons passing through a unit of area per unit of time, typically measured as counts per second per square meter.

Polymer: A large molecule, or macromolecule, composed of many repeated subunits. Polymers range from familiar synthetic plastics such as polystyrene or poly(methyl methacrylate) (PMMA), to natural biopolymers such as DNA and proteins that are fundamental to biological structure and function. Polymers, both natural and synthetic, are created via polymerization of many small molecules, known as monomers. Exemplary polymers include poly(methyl methacrylate) (PMMA), polystyrene, ionoplasts, silicones, epoxy resins, and nail polish.

Self-absorption: The percentage of emitted light from a plurality of fluorophores that is absorbed by the same plurality of fluorophores.

2. Overview

Currently designed STS integrated systems use fiber-coupled tungsten halogen broadband light sources, such as Ocean Optics, HL-2000-HP. These types of broadband light sources are prone to several drawbacks. First of all, current tungsten-halogen bulb light sources are bulky. Secondly, considerable efforts are required to couple sufficient amount of the light into optical fiber. Reflectors and focusing lenses are used to maximize coupling efficiencies. Thirdly, spectral shape is mostly fixed by the color temperature of the light source, and cannot be tuned for optimal performance. Finally, there is a significant warm-up time associated with these bulbs, often 10 s of minutes. Overall, this results in relatively large and expensive fiber coupled units with a number of technical drawbacks for this particular application. These limitations restrict the flexibility of the light source and hinder widespread adoption of STS technology.

A new broadband illumination light source is disclosed herein which may be integrated into optical fibers by utilizing low-cost, low-toxicity bright QDs coupled with an efficient and intense LED to yield broad and tunable emissions. This light source may also be less expensive to produce than those based on conventional technologies.

Colloidal semiconductor nanocrystals, or QDs, are tiny pieces of semiconductor material that are typically less than 20 nm in size. Owing to their small size, these materials have several advantageous properties that include size-tunable PL emission over a wide-range of colors, a strong and broadband absorption, as well as remarkably high PL efficiency. Changing the size of the QDs is also relatively straightforward due to the solution processing techniques used to synthesize the material.

The ability to tune the QD size, and therefore the absorption/emission spectra, allows for flexible fluorescence across the full color spectrum without needing to modify the material composition. As the QD size increases, the absorption onset and PL spectrum shifts to redder wavelengths, while decreasing the size shifts the absorption and PL towards the blue. The size tunability of colloidal QDs is beneficial for STS applications, since modifying the size of QDs and mixing several different sizes allows for easy manipulation of the broadband spectrum. Further, broad absorption of UV-blue light allows for simultaneous excitation of all the QDs with just a single blue or UV LED, which is readily available as a fiber-coupled light source. Bright PL with near unity QYs means that the illumination light source can be made more energy-efficient as well. Finally, the very small size of the nanocrystals also means they can easily be integrated into the optical fibers with minimal scattering, by either inserting them into the hollow-core fibers in liquid solution form, polymerizing it afterwards, or by directly placing the QDs on the tip of the fiber. Using solution synthesis techniques to fabricate QDs means a cost-effective and scalable approach compared to the manufacture of halogen light bulbs and the coupling of halogen bulbs to optical fibers.

Currently, the largest market for colloidal QDs is display applications, where QDs are used to create a pure (red-green-blue) white backlight for improving picture quality and efficiency. This is accomplished by using QDs to efficiently down-convert blue photons emitted from a blue LED, into red and green photons with a narrow emission width. This produces a crisp and eye-catching display, since the red, green and blue colors are very pure and bright.

One problem with current colloidal QD technologies is they utilize material compositions such as cadmium selenide (CdSe), lead sulfide (PbS), or indium phosphide (InP), which are all toxic materials. Along with high manufacturing costs (>$100,000/kg), this aspect of the technology has ultimately limited the application of QDs to markets where the nanocrystals are encapsulated and used in only trace amounts in order to reduce the risk of exposure to people.

The toxicity issues, manufacturing costs, and limited tunability ranges faced by alternative QD technologies present a problem for the use of these technologies in broadband STS illumination light sources. First and foremost, these materials pose significant health risks. In addition, they do not offer price benefits over the current technologies, and typically require more than just a single type of QDs to cover the spectral range of the interest. The preferred embodiments of the devices and methodologies disclosed herein may be utilized to solve these issues, since they utilize extremely bright QDs that are inexpensive to manufacture and do not contain hazardous materials.

At present, the best performing QDs are composed of $CuInS_2/ZnS$. These QDs have the potential to be disruptive in the emerging QD industry, due to their lower manufacturing costs, low toxicity, and (in some cases) better performance. $CuInS_2/ZnS$ beats the typical QD material, such as CdSe or Pb Se, on the critical metrics of toxicity and cost. On other performance metrics, $CuInS_2/ZnS$ QDs are favorable as well. For example, they have a large Stokes shift (~450 meV), which limits self-absorption in the material, and allows higher concentrations of QDs to be used in the optical fibers. Furthermore, broad emission spectra means that fewer different QDs are needed to create a broadband illumination source. For these reasons, the (preferably colloidal) QDs of the preferred embodiments disclosed herein may create a unique opportunity, and may represent the best option for developing a QD-based, fiber-integrated, miniaturized broadband illumination source. Such illumination sources may be especially advantageous in STS applications.

In a preferred embodiment, QDs are provided which are surrounded with a shell. Efforts have thus far been specifically focused on CuInSe$_x$S$_{2-x}$/ZnS QDs, but other semiconductors (e.g., CuGaS$_2$, AgInSe$_2$, etc.) may also be utilized in the devices and methodologies disclosed herein, and may be utilized to extend tunability towards the infrared (IR) and blue regions of the spectrum.

The core material is not new in its bulk form (macro-sized, commonly known as "CIS" or "CIGS"), and has been used to make flexible, non-toxic, thin-film solar cells with >20% conversion efficiency. Because this material is an alloy (that is, x in the above formula may be varied to adjust the band-gap), the optical spectrum may be tuned by composition in addition to size, which enables much greater flexibility. This is particularly attractive in applications where there is an optimal size needed, independent of the spectrum. This feature is also important for STS applications, where both visible and NIR spectral ranges may be required; such ranges are not easily accessible by other QDs compositions without the need to mix several different types of the QDs. Most QDs on the market today are composed of CdSe or PbS, and suffer from at least two major drawbacks, namely, they are expensive (>$10,000/g retail prices) and they are toxic. The I-III-VI QDs disclosed herein are much less expensive compared to other commercialized QD materials such as CdSe and InP, mainly due to the single reactor synthesis that may be used to synthesize them and the attendant, inexpensive precursors. The low-cost manufacturing associated with these QDs, and their use of low-toxic materials, may enable these materials to become ubiquitous throughout markets (such as, for example, STS) that CdSe and InP QDs are not suitable for.

To date, it has been very difficult to realize a low-cost miniature system for STS due to three key challenges. The first of these challenges is the broadband illumination challenge. In order to illuminate the sample under study with a continuous broadband spectrum covering both the visible, near, and shortwave infrared, one has to rely on rather bulky and energy inefficient incandescent or halogen lamps.

The second challenge is the broadband sensitivity challenge. In particular, in order to distinguish between different types of tissues, the spectral tissue sensing device requires a high sensitivity over a broad spectral range (400-1700 nm), which is currently only possible by combining discrete, bulky, and costly spectrometers.

The third challenge is the integration challenge. In particular, there is currently no system that is high-performing and is still fully integrated, miniaturized, and cost-effective.

It is a goal of the present disclosure to solve the broadband illumination challenge using CuInSe$_x$S$_{2-x}$/ZnS quantum dots (QDs) with broad and bright emission as phosphors, and then integrating this technology into the final system to solve the broadband sensitivity and integration challenges. One key differentiator of the preferred materials disclosed herein is the high (>95%) quantum yield (QY) of the QDs in the broad spectral range, which may permit the use of an LED-based, fiber-coupled, broadband illumination source. The added ability to manipulate the shape of the spectrum by adjusting individual QDs (peak wavelengths/concentrations) offers another significant advantage over traditional light sources.

In a preferred embodiment, the luminescent materials utilized herein comprise a plurality of fluorophores (such as, for example, CuInZnSeS quantum dots) which are disposed within or upon a substrate. The fluorophores have a quantum yield greater than 50% and an absorption spectrum with a maximum intensity at wavelengths less than 400 nm, and emit a spectrum of light having a maximum intensity at wavelengths within the range of 400 nm to 1200 nm.

The Broadband Illumination Challenge

In order to illuminate the sample under study with a continuous spectrum covering the visible, near, and shortwave infrared, one has to rely on bulky and inefficient lamps that are too weak to give sufficient signal-to-noise ratios. A miniature, bright, and low-cost fiber-coupled illumination source is highly desired. It is a goal of this disclosure to solve the broadband illumination challenge using CuInSexS$_{2-x}$/ZnS quantum dots (QDs) of the type disclosed herein. These QDs are excited with a blue LED to give broad and bright emission from the visible to NIR. A key feature of this approach is the high (>95%) quantum yield (QY) of these QDs in the broad spectral range, which would allow for an LED-based fiber-coupled broadband illumination source. The added ability to manipulate the shape of the spectrum by adjusting individual QDs (peak wavelengths/concentrations) offers another significant advantage over traditional light sources.

The environmentally friendly and cost-effective CuInSe$_x$S$_{2-x}$/ZnS QDs disclosed herein have advantageous properties over alternative materials, including size-tunable photoluminescence (PL) over a wide range of colors, broadband absorption, very bright PL (QY>95%) and minimal self-absorption and high degree of tunability, from blue-green to NIR. More importantly, the low self-absorption of the QDs will allow for the generation of an intense broadband "white light" spectrum without significant reabsorption.

The broader societal impact of the STS systems and methodologies disclosed herein is at least twofold. First of all, they enable cost-effective, time-saving diagnostics tools, which are critical to the rapid detection of cancers, and thus will result in more prompt and efficient healthcare. Timely intervention of cancers is the first step towards better outcomes, and more saved lives. Secondly, they will provide real-time feedback during surgeries by differentiating between healthy and malignant tissues. This will allow for removal of all malignant tissues, while preserving healthy ones, which will greatly reduce complications during surgery and metastasis and cancer recurrence post-surgery. Better diagnostics and surgery will lead to more lives saved, and thus will positively impact society. Further, reduction in feedback time and recurrence will realize significant savings in terms of patient healthcare.

The systems and methodologies disclosed herein may enable broadly utilized STS by introducing a dramatically reduced (and less expensive) form factor for STS devices, such that the instruments can be implemented widely across hospitals, and can even be supplied to doctor's offices. The ability to provide instantaneous feedback may result in faster medical diagnosis. Widespread adoption of STS technology may allow for the generation of a "smart" database in which millions of spectra may be continuously analyzed to improve the accuracy and specificity of the diagnosis. Ultimately, use of this class of devices may improve public health due to its ability to enable doctors to prescribe accurate and specific treatment plans based on STS data. Overall, the development of a broadband light source for STS using QDs of the type disclosed herein may not only reduce costs for patients, doctors, and insurance companies, but may reduce the time intervals between the initial tests, diagnostics and surgery, which may save many lives. Finally, due to their low toxicity, the QDs that may be used in light source do not pose the environmental, health, or safety (EH&S) concerns that would be posed by other QD materials.

The total economic losses resulting from cancer treatment-associated costs and indirect mortality expenses are growing constantly and currently surpass $200 billion. Therefore, it is critically important to diagnose cancer at its earliest, most treatable stage to give patients the greatest chance for survival with the fewest health complications. The research firm Future Market Insights predicted in January of 2017 that the global biopsy devices market will grow at a 6.5% CAGR over the time period 2016-2026, and will be worth more than $2.7B in 2026. Furthermore, they estimate that needles make up 37.6% of revenue in 2016, and will be worth $960M by 2026. Ideally, traditional biopsy needles may be replaced by "photonic needles" to improve needle accuracy and provide instantaneous feedback. Each of these photonic needles may require a broadband light source for STS measurements. Alternatively, the broadband light source may be incorporated before the disposable needle in a segment of optical fiber, which will be interchangeable and tunable for the needs specific to applications.

The Integrated Spectrometers for Spectral Tissue Sensing (InSPECT) consortium identifies the broadband illumination challenge (the ability to illuminate the sample under study with an efficient continuous broadband spectrum, covering both the visible, near and shortwave infrared) as the first of the key challenges of the technology. Other important applications for the broadband light source include, but are not limited to, (a) the identification of lymph nodes, ensuring full resection of cancerous and diseased tissue during surgery to avoid the need for additional surgeries, and (b) the illumination of molecular agents injected in the body which bind to specific cell types and which exhibit emission under specific light sources. The broadband QD-based light sources disclosed herein may enable the InSPECT system (along with other systems that may be developed in the art) to use these light sources, and to enjoy significant device penetration in the marketplace, including the needle market.

The biomedical and bioimaging industries offer a substantial growing market for low-toxicity QD-based technologies. As of February 2017, one subset of these industries—the biomarker market—was estimated to be worth $28B in 2016, and was forecast to grow to $54B by 2021. Currently, organic dyes, fluorescent proteins, and toxic QDs, such as those based on CdSe, dominate the market. However, for STS broadband light source applications, all of the current solutions lack performance towards the MR spectral range. Bulky light bulbs (tungsten halogen) are used as the illumination source, but they have low efficiency and are hard to couple to fiber-optics. Inexpensive $CuInSe_xS_{2-x}$/ZnS QDs with almost unity QYs may be excited by fiber-coupled LEDs, and may be integrated with the fiber, thus solving the efficiency, price, and miniaturization issues.

Conventional light sources in the STS illumination market include incandescent and halogen bulbs, other types of QDs, and NIR phosphors. With respect to traditional light bulbs, the illumination technologies disclosed herein are expected to compete primarily on miniaturization, intensity (fiber coupling), and efficiency, and are expected to remain an inexpensive approach. Other types of QDs are toxic, and do not have PL tunable across the desired spectral range. Moreover, the small stokes shifts of the CdSe- and PbSe-based QDs would result in a large amount of reabsorption, dramatically decreasing the device efficiency. NIR phosphors are underdeveloped, and typically have poor efficiencies. In addition, at least four different phosphor compositions would be required in order to satisfy the requirements of broad band emission (vis-NIR), complicating device assembly and the supply chain. $CuInSe_xS_{2-x}$/ZnS QDs have another distinct advantage over phosphors in that they can be easily tuned from the visible to NIR based on size and composition, thus allowing one to easily manipulate the output spectrum. Phosphor emission is largely fixed and is based on dopant energy levels, with no design freedom. It will be appreciated from the above table that the $CuInSe_xS_{2-x}$/ZnS QDs disclosed herein may be superior in all categories, and may enable an STS device with improved performance. At present, preliminary estimates suggest that each of the broadband illumination light source will require no more than 10 mg of various $CuInSe_xS_{2-x}$/ZnS QDs.

There are at least four direct applications that could benefit from the development of a compact, intense, broad band light source. These include (1) spectral tissue sensing at needle tip during tumor biopsy; (2) identification of lymph nodes for resection for cancer staging; (3) ensuring full resection of cancerous tissue during surgery, and (4) excitation of fluorescent agents in the body for identification of specific cell types. The signal-to-noise ratios encountered in current technologies are inadequate for wide-spread adoption, and an improvement in the light source would help deliver the improvement required to see the technology blossom. The devices and methodologies disclosed herein are expected to be beneficial to multiple areas of spectral analysis, due to their potential to deliver intense, broadband light in a compact package.

It is an object of the present disclosure to provide bright $CuInSe_xS_{2-x}$/ZnS QDs across the entire spectral range of interest. Thanks to previous efforts involving the development of solid-state-lighting and luminescent solar concentrators (see, e.g., DOE SBIR DE-SC0015184 and NSF SBIR IIP-1622211), the photoluminescence (PL) quantum yields (QYs) of QDs have been enhanced in the red (600-700 nm) and in part of the NIR (~800-1000 nm) spectral ranges from <50% to >95%. The QY values at short wavelengths (~550 nm peak) and long wavelengths (>1000 nm) still require some improvement, although this is primarily due to insufficient demand heretofore to work on development of these spectral regions. The next important milestone related to QD performance will be the development of a mixture of QDs (several sizes and/or compositions) to achieve a broadband STS light source that still maintains high QY, especially as the NIR emission range is extended towards 1500 nm.

It is also an object of the present disclosure to provide for the integration of these QDs into optical fibers for a high intensity, reliable illumination source. The simplest approach may be based on incorporation of the QDs in liquid solution into hollow fibers, which may be spliced directly to the output fiber of the blue excitation LED. This platform may be readily used to validate the product and to optimize it by varying the amount of QDs, their concentrations, and volumes. This platform may be further used for the co-development of the final STS products. For the final product, however, alternatives, such as polymerization of the PMMA containing QDs inside the hollow fibers or placing QDs on the tip of the fiber, may be utilized. Alternatively, a light source can be composed of several miniature (~1×1×0.1 cm) pieces of polymer—a version of a luminescent solar concentrator (LSC); with optical fibers incorporated into the same polymers and then combined into a single output. The QDs can be excited by a simple and cheap blue LED (such as ChanZon 10DGL-DZ-3W-BL, $7 for 10 pcs). The PL concentrated in the LSCs gets coupled into the optical fibers and delivered to the output. This simple prototype allows for unique tunable light source: by combining several small LSCs with individually-colored QDs and allowing independent control over the excitation power for each of them, one gets a miniature, yet highly flexible broadband light source. For example, the output spectrum can be easily modified to compensate for the drop of the sensitivity of Si detectors around 1000-1100 nm.

3. Description of Specific Embodiments

It is a goal of the present disclosure to create a new fiber-integrated broadband illumination source for STS applications. It has previously been demonstrated that hollow-core optical fibers may be utilized to contain liquids of various chromophores for photonics applications. This methodology was later utilized to conduct characterization of weak third-order nonlinear effects in liquid solutions. An important aspect of this technology is the ability to perform fusion splicing of the liquid core optical fiber to standard single-mode optical fibers. This ability makes the technology both fully integrated and practical, which are major challenges that had previously significantly hindered progress in liquid-photonic applications. This advantage allows for the combination of various segments (and numbers of segments) of the hollow-core fibers in various sequences (including embodiments where one or more segment type repeats) and with different segment lengths, QD sizes, concentrations, and the like, making this a flexible platform for testing STS broadband illumination sources.

In order to satisfy an industry need for a broadband light source that is low-cost, miniaturized, fiber-integrated, and bright, systems and methodologies are disclosed herein which are based on $CuInSe_xS_{2-x}/ZnS$ QDs. Due to their minimal self-absorption, bright and broadband PL, and color tunable optical properties, $CuInSe_xS_{2-x}/ZnS$ QDs are a unique alternative to traditional halogen light bulbs. The QD-based light source differs from traditional bulbs in that its output spectrum may be tuned by modifying the peak emissions and concentrations of the constituent QDs to produce the optimal illumination spectrum. More specifically, this may help to increase the signal-to-noise ratio of the detection by equilibrating the difference of sensitivities of the Si-based and InGaAs-based spectrometers. Furthermore, the differences in spectral sensitivity for each individual spectrometer may be compensated for by changing the illumination spectral density.

Several approaches exist to use QDs as broadband illumination light sources. First, the broadband spectrum may be generated by mixing QDs of different size that emit over a range of wavelengths to generate the broad spectrum. However, this approach has a drawback in that the short wavelength portion of the emission spectrum will be reabsorbed by QDs emitting at longer wavelengths if the concentrations of the QDs is high, which is likely to be required for the bright light source. The low self-absorption of the preferred QDs disclosed herein provides quantifiable benefits in terms of addressing this problem.

An alternative approach is also possible which features the arrangement of differently sized/composed QDs in segments along the optical fiber, with NIR QDs being next to the excitation LED, and visible QDs being closer to the light source output. This approach almost completely avoids the problem of reabsorption. The length of each segment, and the QDs concentration within each segment, may be used to control the output spectrum. Liquid-core optical fibers demonstrated earlier may represent an ideal test platform for this approach. The segments of fibers with various QDs can be manufactured and combined together to determine optimal conditions. Further, QDs with two distinct emission peaks as far as 200 nm apart from each other can be mixed in the same segment without reabsorption to simplify the design. The length of each segment and QDs concentration within each segment may be used to control the output spectrum. Currently, when dispersed at 0.1 wt %, a preferred embodiment of the QDs disclosed herein absorb 90% to 99% of the incident light over 1 cm pathlength, depending on the PL wavelength. This means that combining pairs of different QDs into three-to-four segments of the length ~0.2-0.5 cm is sufficient to convert blue/UV LED light into the broadband spectrum, without any significant waveguiding losses. Using appropriate parameters for the desired light source, the monomer solutions of the QDs may be prepared and then polymerized inside the hollow-core fibers to create a reliable product. Alternatively, QDs in polymers may be placed into optical fibers.

Preliminary tests have been conducted to verify that the QDs described herein may be used as a broadband illumination source. Twelve QDs with different peak PL wavelengths ranging from 550 nm to 1230 nm were selected. Their individual normalized PL spectra span the entire spectral range from 500 to 1500 nm. Once the mixture of QDs is placed in a single cuvette, the broadband PL may be excited using 455-nm fiber-coupled LED. By modifying the concentration of the QDs with visible emission, one may control the visible part of the spectrum.

Further, the NIR tail of the spectrum may also be manipulated by modifying the concentration of NIR-emitting QDs. This, however, also affects reabsorption of the visible PL, and results in somewhat reduced overall brightness (typically by about 15%). Cuvettes with the mixture of QDs appear somewhat yellow under the blue light. This is also observed in the PL spectrum at ~500 nm, highlighting the need for further optimization of the green QDs. One may also see that the spectra have maxima at about 900-1000 nm, and drop at longer wavelengths, which highlights the need for brighter 1000-1230 nm QDs as well. In order for the QD solution to be a drop-in substitute to the currently used light source, it will need to output a similar optical spectrum. The spectrum of the Ocean Optics HL-2000-HP-FHSA halogen bulb (data from the manufacturer) shows differences between the spectra and highlights the need to further optimize some QD wavelengths.

Finally, a photograph of the 8 vials of different QDs with blue fiber-coupled LED excitation source was tested. The NIR-emitting QDs are close to the excitation source, while the visible-emitting QDs are further away. The light from the LED is only partially absorbed in the vials containing IR QDs, while some of the LED excitation light is transmitted through all the vials and excites PL in the visible QDs. This confirms that intelligent design of optical elements containing QDs in series is a viable option in creating a broadband illumination spectrum.

It is desirable to optimize QDs mixtures for the target broadband spectrum (~500-1600 nm). Currently, thanks to previous R&D efforts, bright QDs (QY>95%) exist with PL ranging from 590 nm to 1000 nm. During optimization, the main non-radiative recombination pathways have been eliminated, and the QDs have been successfully engineered to avoid these inefficiencies.

It is expected that similar non-radiative pathways dominate at all wavelengths, and thus, the lessons previously learned during optimization of the QDs are expected to be directly applicable to other wavelengths as well. Several parameters that are detrimental for achieving high QY have been investigated, such as elemental stoichiometry, synthesis temperature and growth period, shell growth precursors, etc. Some or all of these parameters may need to be optimized at each wavelength in order to achieve the brightest possible spectrum across the entire tuning range.

It is a goal of this disclosure to determine the optimal combination of QD sizes and compositions to achieve a relatively flat broadband NIR spectrum. This includes a focused effort to shift emission to 1300 nm, with QY>50%. With a peak position at 1300 nm, it is expected that the tail of the emission peak will still provide significant light at 1600 nm, which will be required for tissue characterization applications.

Existing materials may be combined (a few sizes/compositions vs many) in various arrangements (all mixed together vs segmented) to determine the form of the minimum viable product. So far, preliminary tests show that 12 samples, with about a 50 to 100 nm distance between the emission peaks, is sufficient to create a smooth broadband spectrum, though it is expected that similar results may be achieved with fewer combined materials. Minimizing the number of the QDs simplifies the device and reduces reabsorption issues. Therefore, it will typically be important in an application to investigate the minimum number of samples necessary to achieve a continuous spectrum.

In order to incorporate QDs into optical fibers, several unknowns typically need to be resolved. In addition to incorporating individual solutions into hollow core fibers, the optimal concentrations of each individual QDs may need to be determined. Further, depending on the design required to achieve maximum brightness, the optimal length of each fiber segment or the length of the fiber for the QD mixture may need to be determined. Initially, this information may be obtained (at least partially) by using solutions of the QDs. However, final optimization will preferably take place on the actual optical fibers. Although procedures for infilling hollow-core optical fibers are currently known in the art, additional methodologies may need to be be developed.

Working prototypes of broadband illumination sources may be built based on the principles disclosed herein. The brightness of these illumination sources may be examined and compared to existing halogen bulbs, and factors which limit the brightness of these light sources may be isolated and improved upon. After sufficiently bright light sources are designed and created, their utility in the characterization of tissue samples may be demonstrated. Model solutions may be used to demonstrate that the light source can differentiate between water and lipids, and can determine their relative concentrations.

Figure 3:
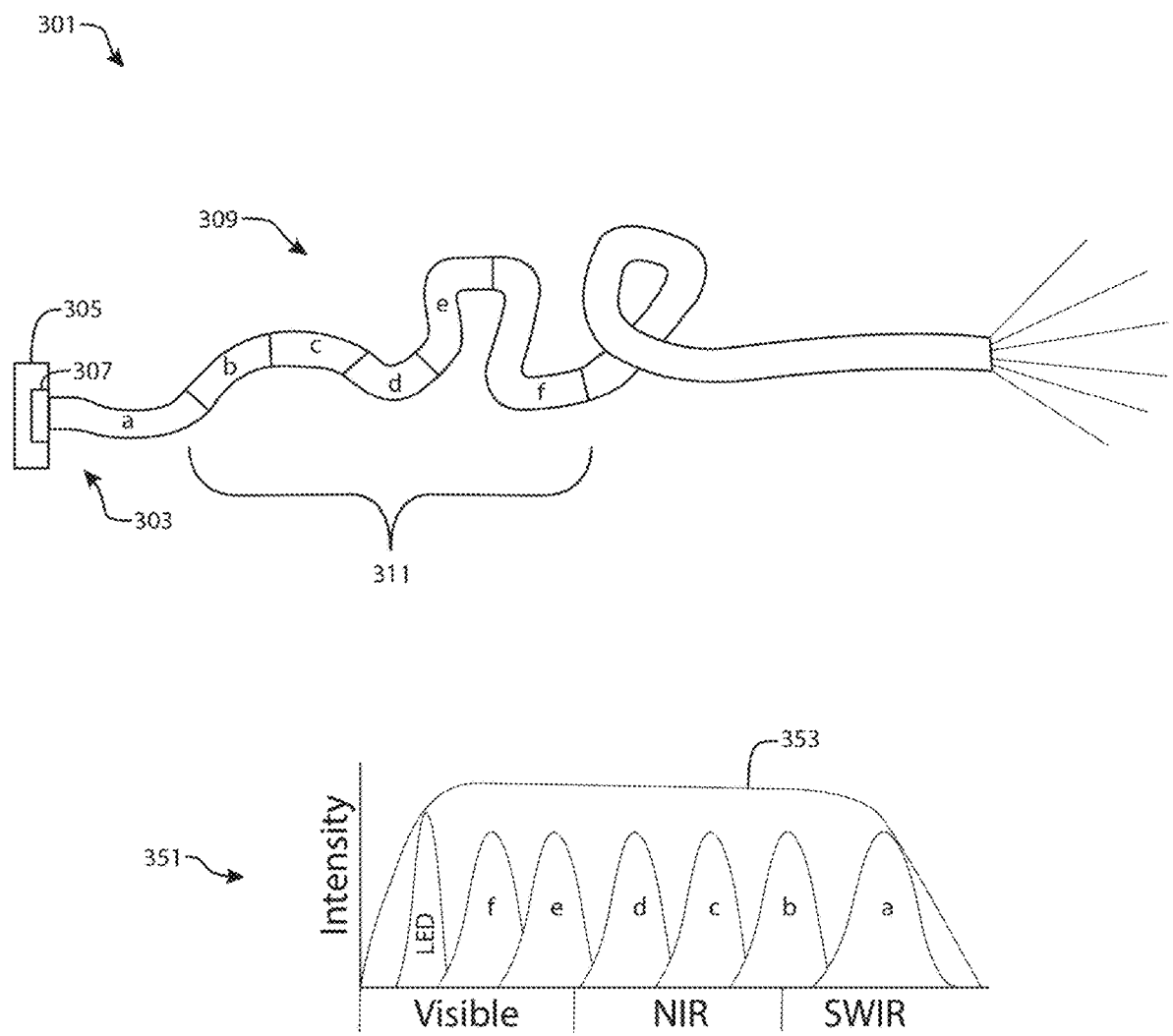
FIG. 3 is a schematic that depicts one mode of the invention wherein a blue light excites at the end of a fiber that contains fluorophore segments emitting at progressively longer wavelengths to cover the visible to NIR. This mode limits self-absorbance, and minimizes the number of LEDs required, and hence minimizes the device size.

The present disclosure provides a light source which may be utilized in medical diagnostic equipment such as STS. In a preferred embodiment, it begins with a high-powered UV or blue LED which is optically coupled to a fiber optical cable. The schematic in FIG. 3 depicts the case wherein a blue light excites various fiber segments containing QDs emitting at progressively longer wavelengths to cover the visible to NIR. The blue/UV LED light source may be optically coupled to the end of the optical fiber as depicted in FIG. 3, or along the length of the fiber. The resulting spectrum may be both intense and continuous over the range of interest to the medical diagnostic market. The light source disclosed herein may provide the following various advantages over existing technologies in this area. These advantages may include any of the following.

Miniaturized and cheap: In an effort to miniaturize and reduce the price of this component, the existing light source (halogen light source) may be replaced with readily available LED sources (UV or blue). These LED sources may be utilized to provide the excitation source for a QD-integrated optical fiber.

High powered broad band illumination: The optical fiber containing the QDs disclosed herein may provide bright and efficient broadband illumination when excited by blue or UV light. The disclosed QDs may have many advantageous optical properties such as high efficiency (>95%, under ideal conditions), low self-absorption, and tunability across the wavelength range of interest. These properties, along with intelligent selection of a high-powered LED source, may result in high intensity illumination.

Spectral tunability: Due to the properties of the preferred QDs disclosed herein, custom light output may be possible. Spectral requirements are expected to be application specific, and using QDs allows for an easily customized spectral output based on QD size/composition, concentration, and fiber length.

Flexible integration: Such fiber-integrated light sources have the advantage of integration flexibility (that is, they may be integrated at any point in the fiber optic light path). The QD-containing fiber may be located next to the LED or at the connection between the fiber optic and the needle, or could even be integrated in the needle itself. Depending on the application, regulations for the product can vary significantly, but all scenarios will be considered.

FIG. 1 depicts a particular, non-limiting embodiment of a high power LED light source 101 in accordance with the teachings herein, and which may be utilized in medical diagnostic equipment such as STS. The LED light source 101 in this particular embodiment includes an LED fixture 105 comprising a plurality of blue/UV LEDs 107 and an optical fiber 109. The optical fiber 109 includes a first segment 111 in which a mixture of chromophores b, c, d, e and f have been have been mixed or compounded into the polymeric resin used to fabricate the first segment 111, and a second segment 113 which is devoid of any chromophores.

The emissions spectra 151 of the LED light source 101 is also depicted, and includes emissions peaks corresponding to chromophores b, c, d, e and f, as well as the material a of the second segment 113 of the optical fiber 109. The peak corresponding to the LEDs 107 from the light fixture (denoted "LED") is also indicated, as is the cumulative emissions spectrum 153.

In operation, the LED light source 101 excites various fiber segments containing QDs emitting at progressively longer wavelengths to cover the visible to NIR. The LED light source 101 may be optically coupled to the end of the optical fiber as depicted in FIG. 3, or along the length of the fiber. The resulting spectrum may be both intense and continuous over the range of interest to the medical diagnostic market. Embodiments of the LED light source 101 depicted may be produced which are bright and compact, and provide broad-band illumination.

Figure 2:
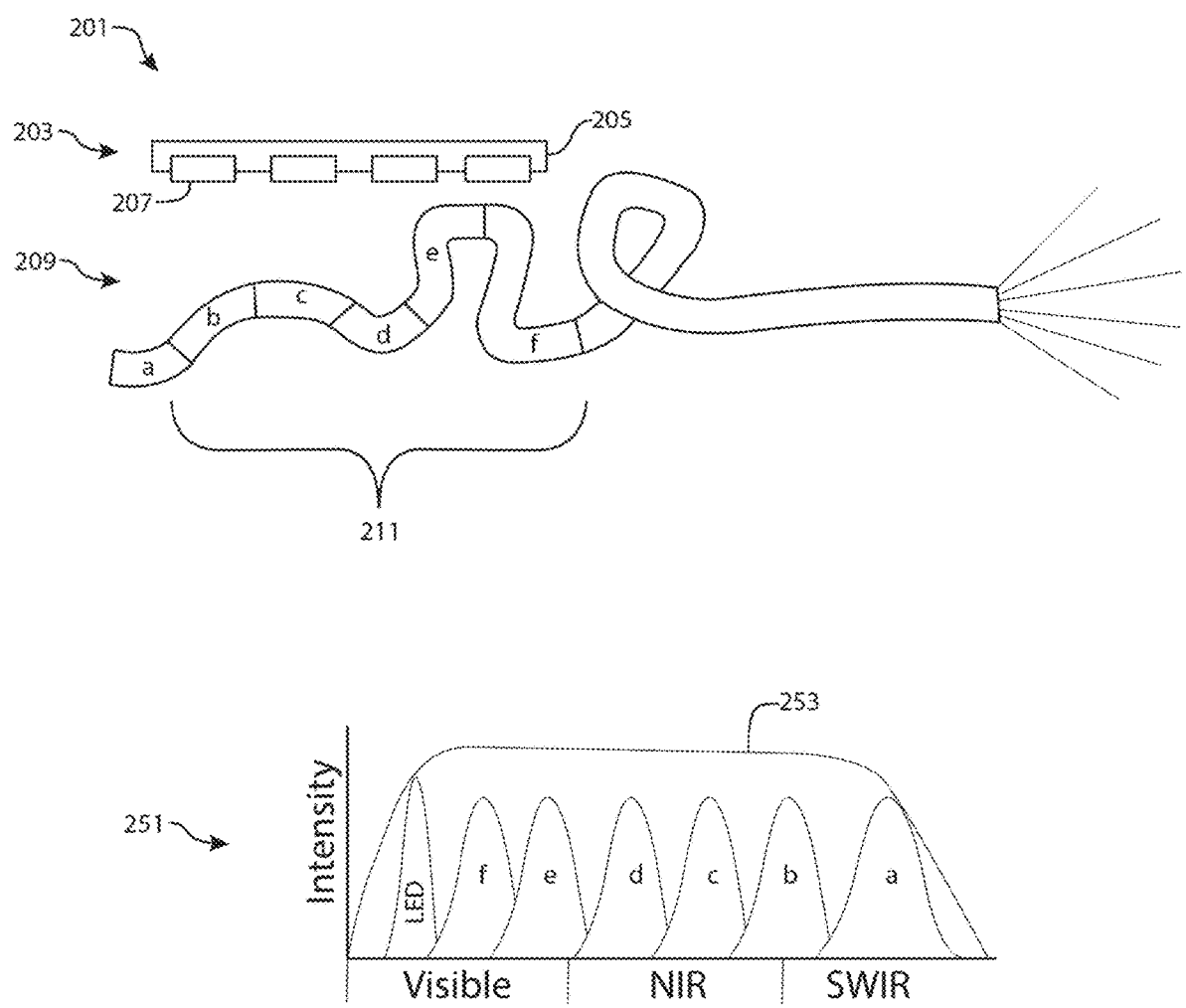
FIG. 2 is a schematic that depicts one mode of the invention wherein a blue light excites along a fluorophore-integrated fiber having segments emitting at progressively longer wavelengths to cover the visible to NIR. This mode limits self-absorbance.

FIG. 2 depicts another particular, non-limiting embodiment of a high power LED light source 201 in accordance with the teachings herein, and which may also be utilized in medical diagnostic equipment such as STS. The LED light source 201 in this particular embodiment includes an LED fixture 205 comprising a plurality of blue/UV LEDs 207 and an optical fiber 209. The optical fiber 209 includes a first segment 211 having subsegments a, b, c, d, e and f in which chromophores a, b, c, d, e and f have respectively been mixed or compounded into the polymeric resin used to fabricate the first segment 211. The optical fiber 209 further includes a second segment 213 which is devoid of any chromophores. The LED light source 201 may be configured to provide the same or similar advantages as those provided by the LED light source 101 of FIG. 1, and may have the same or similar emissions spectra 251.

FIG. 3 depicts another particular, non-limiting embodiment of a high power LED light source 301 in accordance with the teachings herein, and which may also be utilized in medical diagnostic equipment such as STS. The LED light source 301 in this particular embodiment includes a blue/UV LED fixture 305 and an optical fiber 309. The LED fixture 305 in this embodiment is directly coupled to the optical fiber 309.

The optical fiber 309 includes a first segment 311 having subsegments b, c, d, e and f in which chromophores b, c, d, e and f have respectively been mixed or compounded into the polymeric resin used to fabricate the first segment 311. The optical fiber 309 further includes a second segment 313 which is devoid of any chromophores. The LED light source 301 may be configured to provide the same or similar advantages as those provided by the LED light source 201 of FIG. 2, and may have the same or similar emissions spectra 351.

Figure 4:
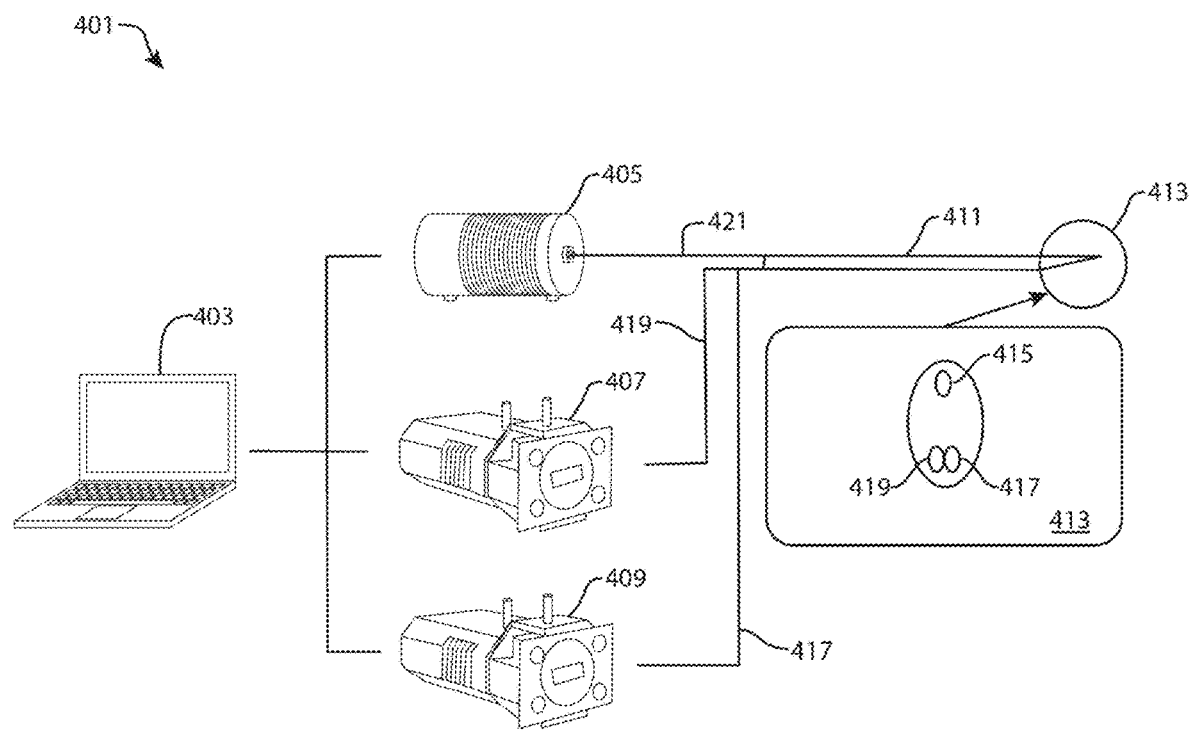
FIG. 4 is a sketch of the current STS optical setup: it consists of a halogen lamp that is connected to a fiber and two spectrometers that are connected to two separate fibers that are located next to each other at the tip of the probe. Taken from Nachabé, R.; Hendriks, B. H. W.; van der Voort, M.; Desjardins, A. E.; Sterenborg, H. J. C. M. Estimation of Biological Chromophores using Diffuse Optical Spectroscopy: Benefit of Extending the UV-VIS Wavelength Range to Include 1000 to 1600 nm. Opt. Expr. 2010, 18, 1432-1442.

FIG. 4 depicts a particular, non-limiting embodiment of an STS optical setup 401 which may be utilized in the systems and methodologies described herein. This optical set-up is based on the set-up described in Nachabé, R.; Hendriks, B. H. W.; van der Voort, M.; Desjardins, A. E.; Sterenborg, H. J. C. M. Estimation of Biological Chromophores using Diffuse Optical Spectroscopy: Benefit of Extending the UV-VIS Wavelength Range to Include 1000 to 1600 nm. *Opt. Expr.* 2010, 18, 1432-1442, which is incorporated herein by reference in its entirety.

The STS optical setup 401 includes a light source 405 (preferably a halogen lamp), a visible spectrometer 407 and an infrared spectrometer 409, all of which are under control of a computer 403. The STS optical setup 401 further includes an optical probe 411. As seen in magnified REGION 413, the optical probe 411 (and specifically, the tip thereof) is equipped with an illumination fiber 415 which is in optical communication with the light source 405, a VIS detection fiber 419 which is in optical communication with visible spectrometer 407, and an IR detection fiber 417 which is in optical communication with infrared spectrometer 409.

Figure 5:
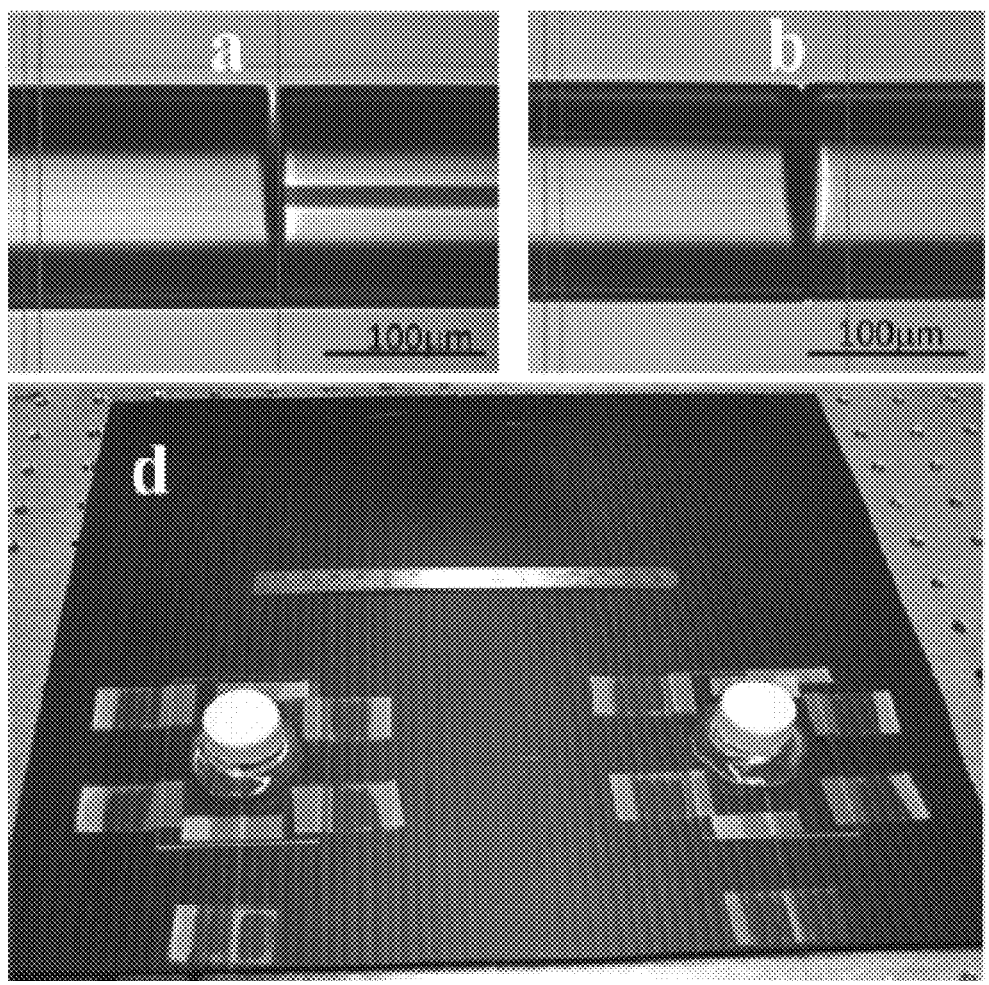
FIGS. 5-6 depict an integrated liquid-core-optical-fiber (LCOF) preparation and stimulated Raman generation setup. a, Gap-splice between Corning SMF28 (left) and a 10 μm core LCOF (right). b, Gap-splice between two segments of Corning SMF28. c, Liquid access port assembly. d, Photograph of an integrated 1 m long LCOF filled with CS2. e, Schematic of an integrated LCOF filled with CS2. f, Schematic diagram of the experimental setup. PBS: polarizing beam splitter; MO: microscope objective; PD: photodiode; OSA: optical spectrum analyzer. Taken from Kieu, K.; Schneebeli, L.; Norwood, R. A.; Peyghambarian, N. Integrated Liquid-Core Optical Fibers for Ultra-Efficient Nonlinear Liquid Photonics. Opt. Expr. 2012, 20, 8148-8154.
Figure 6:
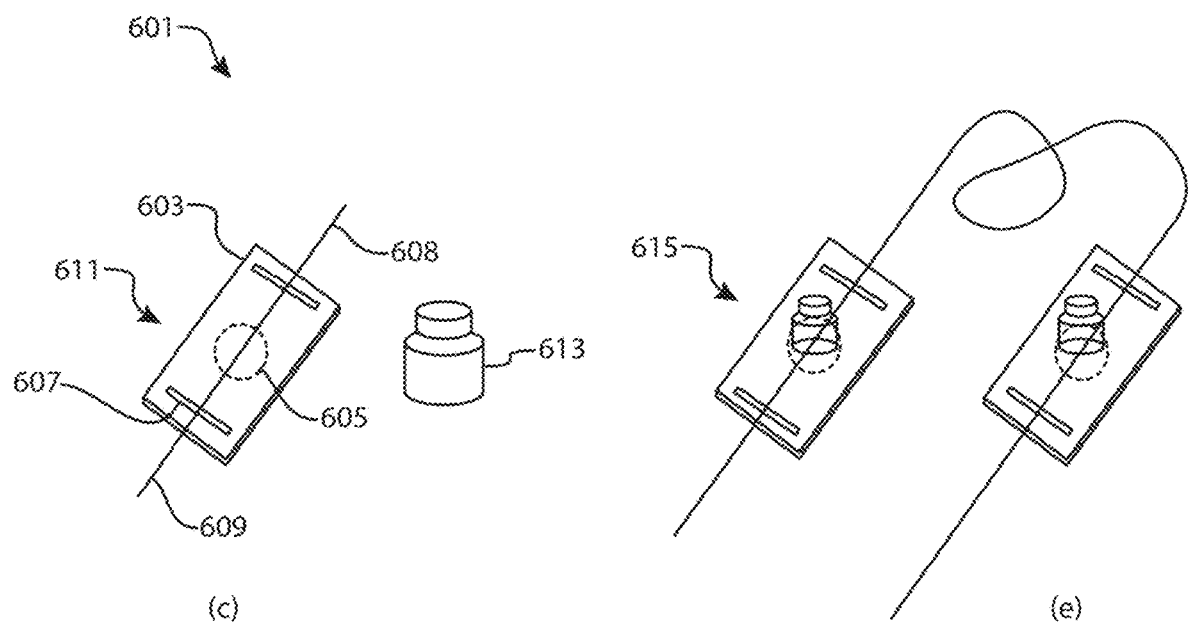
Figure 6:
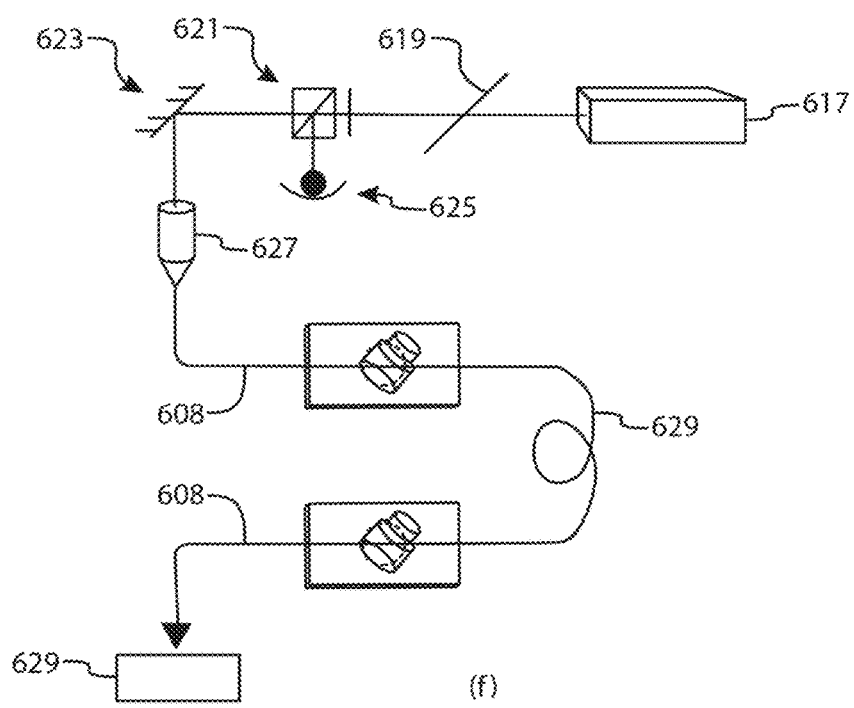

FIGS. 5-6 depict a particular, non-limiting embodiment of an assembly 601 featuring an integrated liquid-core-optical-fiber (LCOF) and stimulated Raman generation, and a process for making the same. This process and assembly are based on those described in Kieu, K.; Schneebeli, L.; Norwood, R. A.; Peyghambarian, N. Integrated Liquid-Core Optical Fibers for Ultra-Efficient Nonlinear Liquid Photonics. *Opt. Expr.* 2012, 20, 8148-8154, which is incorporated herein by reference in its entirety. An image of a gap-splice between a single mode fiber (Corning SMF28) and a 10 μm a liquid core optical fiber (LCOF) is depicted in FIG. 5a. A photo of a gap-splice between two segments of single mode fiber (Corning SMF28 fiber) is depicted in FIG. 5b.

FIG. 6c depicts the fabrication of an optical subassembly 611 having a liquid access port for incorporation into the assembly 601. As seen therein, the optical subassembly 611 comprises an LCOF 608 (here with a 10 μm core) and a standard single mode fiber 609 (here, Corning SMF28) which are joined across a gap splice 605. Each of the LCOF 608 and the standard single mode fiber 609 are mounted on a microscope slide 603 with a portion of adhesive tape 607. Liquid access is provided by way of a liquid medium disposed in container 613. Various liquid media may be utilized for this purpose, although the use of $CS_2$ is preferred.

FIG. 6e depicts the assembly of an integrated LCOF 608 filled with $CS_2$, which is produced by a similar process. A photograph of an integrated 1 m long LCOF filled with $CS_2$ is shown in FIG. 5d.

As seen in FIG. 6f, the assembly 601 produced by the foregoing methods includes a laser 617, a dichroic (or IR) filter 619, a polarizing beam splitter (PBS) 621, a photodiode (PD) 625, a gold-coated mirror 623, a microscope objective (MO) 627, and an optical spectrum analyzer (OSA) 629. The assembly 601 further includes portions of the LCOF 608 and the standard single mode fiber 609 noted above.

Figure 7:
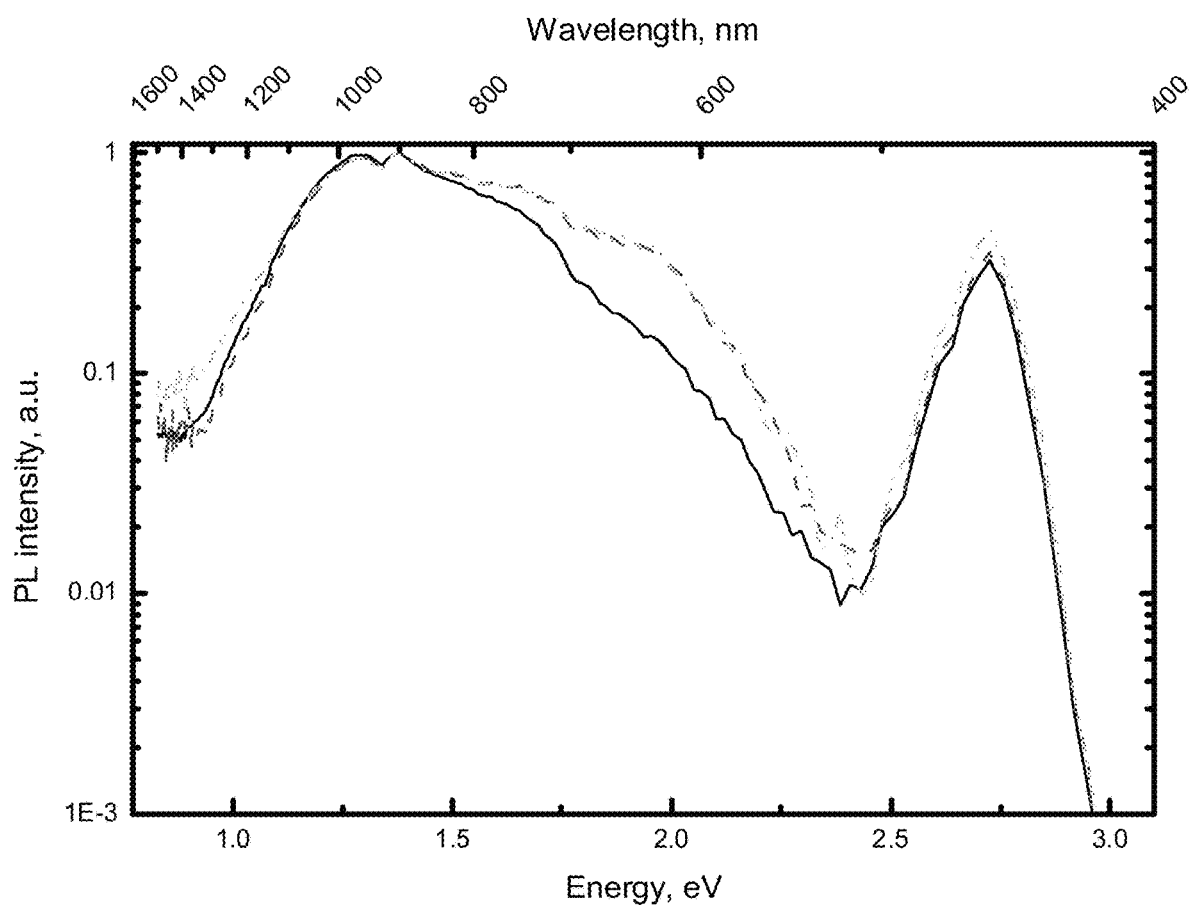
FIG. 7 depicts mixing QDs in different concentrations allows for tunable broadband spectrum.

FIG. 7 depicts the results which may be achieved by mixing QDs in different concentrations. The results depicted are for three different mixtures of QDs produced in this manner. As seen from the variations in the emissions spectra depicted therein, this approach may be utilized to produce a tunable broadband spectrum.

Figure 8:
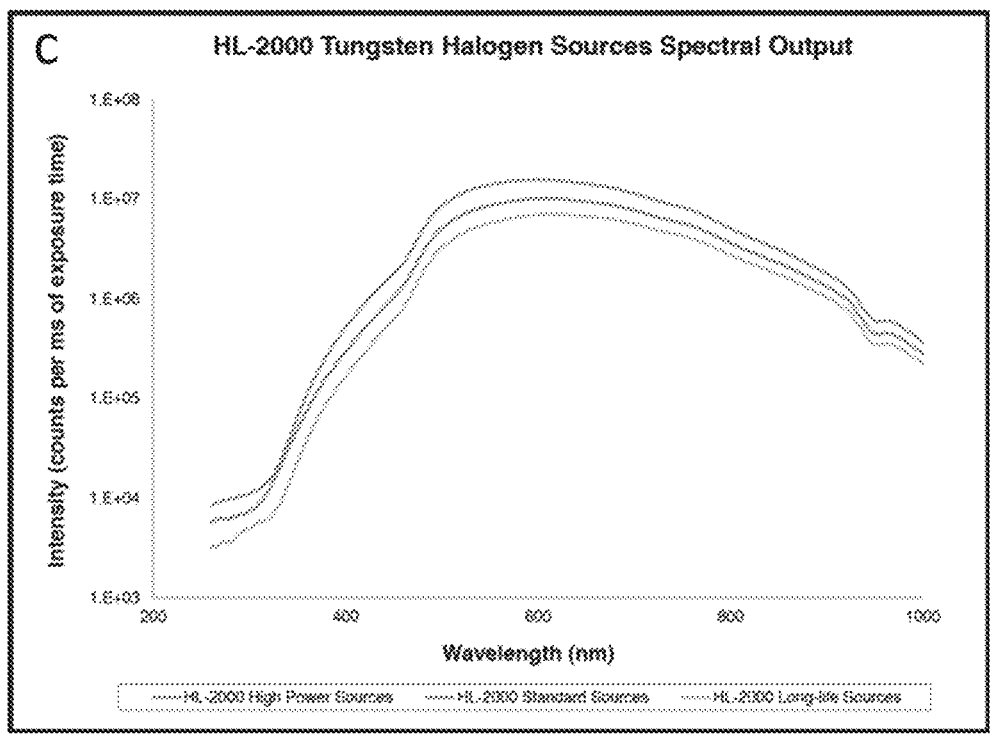
FIG. 8 depicts a spectrum of the Ocean Optics HL-2000-HP-FHSA (from manufacturer).

FIG. 8 depicts a spectrum (obtained from the manufacturer) of Ocean Optics HL-2000-HP-FHSA tungsten halogen light sources. As seen therein, these light sources produce varying output spectra, depending on whether the light source is configured as a high power source, a standard source or a long-life source.

Figure 9:
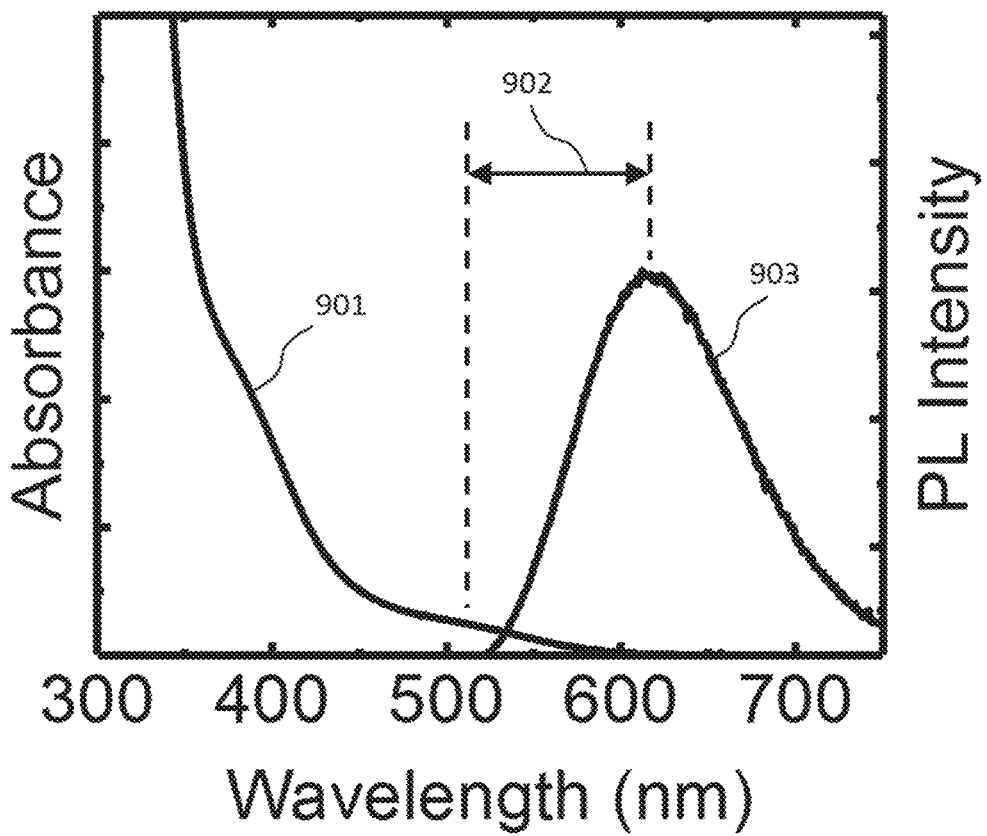
FIG. 9 is a graph of a typical absorption and photoluminescence spectra for $CuInS_2/ZnS$ quantum dots. These QDs are substantially free of toxic elements and are believed to be non-carcinogenic. The QDs can have an emission quantum yield of >90%. These QDs have an absorption spectrum with a maximum intensity at wavelengths less than 400 nm.

FIG. 9 is a typical absorption 901 and photoluminescence 903 spectra for CuInZnSeS quantum dots, which are a preferred fluorophore in the devices and methodologies disclosed herein. These QDs are substantially free of toxic elements, and are believed to be non-carcinogenic. Moreover, these QDs may have an emission quantum yield in excess of 70%, or greater than 90%, and have an absorption spectrum with a maximum intensity at wavelengths less than 400 nm.

As seen in FIG. 9, CuInZnSeS quantum dots can be made to have minimal overlap 902 between their absorption 901 and photoluminescence 903 peaks. As a result, very little of the radiation emitted by these quantum dots as a result of fluorescence undergoes subsequent reabsorption. Moreover, CuInZnSeS quantum dots can be fabricated with absorption peaks outside of the visible region (typically within the UV region), and emission spectra within it. Consequently, the photoluminescence process that these quantum dots undergo has the effect of converting a portion of the incident UV or blue radiation into visible-NIR wavelengths, thus making them ideal for medical applications.

Figure 10:
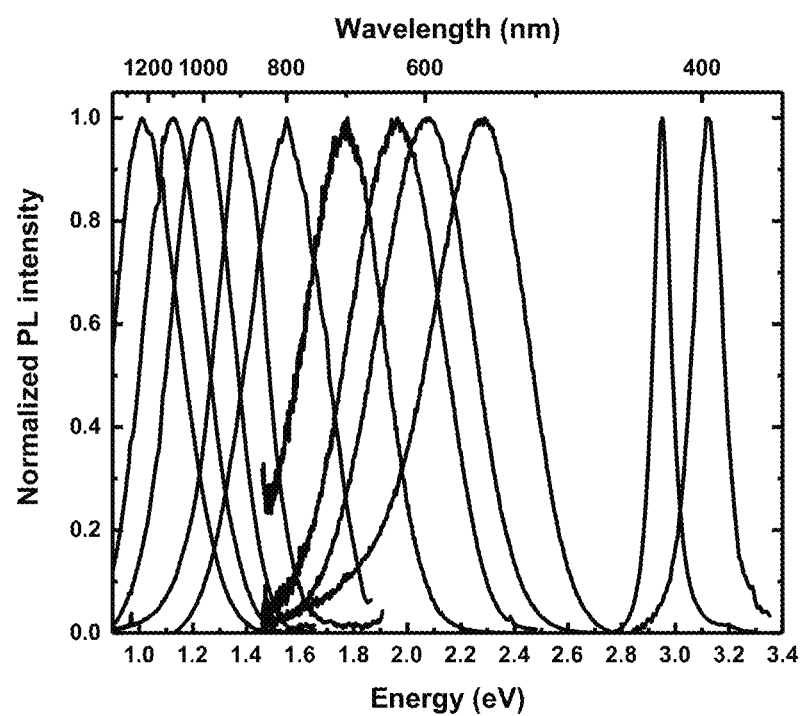
FIG. 10 is a graph of the photoluminescence spectra arising from different sizes and compositions of quantum dots composed of $CuInS_2$, $CuInSe_2$, ZnS, ZnSe, and combinations thereof. The accessible peak emissions with these materials is 400 nm-1200 nm.

FIG. 10 is a graph of the photoluminescence spectra arising from different sizes and compositions of quantum dots composed of $CuInS_2$, $CuInSe_2$, ZnS, ZnSe, and combinations thereof. As seen therein, these materials provide accessible peak emissions within the range of 400 nm-1200 nm.

Figure 11:
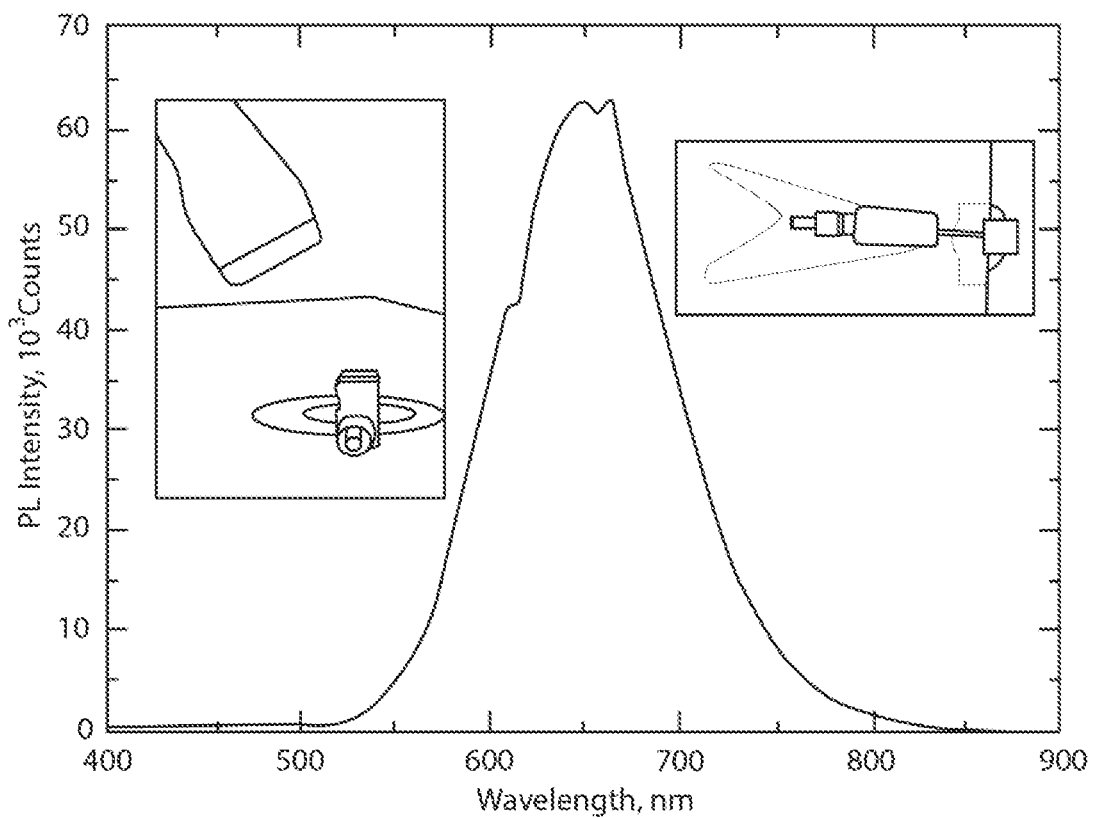
FIG. 11 is a graph of the photoluminescence spectra arising from a prototype fiber-coupled light source (shown in insets, top corners of the graphs). Only one size of QDs is used in the prototype. The optical fiber attached to the prototype is connected to a a Thorlabs SMA fiber adapter. The output of the device is measured suing fiber-coupled spectrometer at a short (1.5 ms) integration time. Photos of the device excited by a blue LED (left; bright red dot at the end of the Thorlabs fiber adapter confirms coupling), and small ChanZon LED (right; bright red light at the left comes out of the fiber adapter after coupling from QDs to the fiber).

FIG. 11 is a graph of the photoluminescence spectra arising from a prototype fiber-coupled light source. Only one size of QDs is used in the prototype used to generate these spectra. The optical fiber attached to the prototype is connected to a Thorlabs SMA fiber adapter. The output of the device is measured suing fiber-coupled spectrometer at a short (1.5 ms) integration time. Photos of the device excited by a blue LED revealed a bright red dot at the end of the Thorlabs fiber adapter, thus confirming coupling. Photos of the device excited by a small ChanZon LED showed bright red light coming out of the fiber adapter after coupling from QDs to the fiber.

Figure 12:
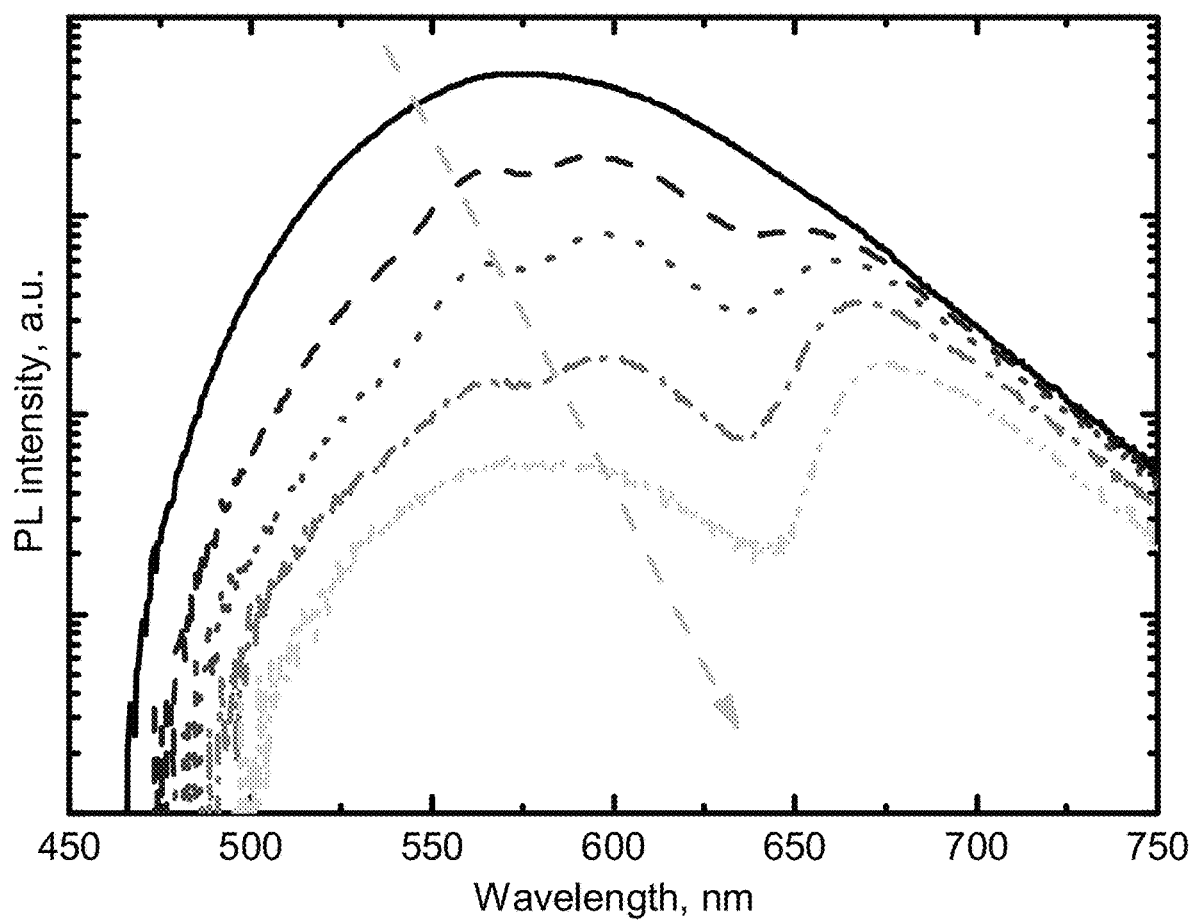
FIG. 12 is a graph showing that the broadband PL of 590-nm QDs is significantly altered upon propagation through bovine hemoglobin in a biological buffer. Depth and concentration information can be extracted by analysis of these spectra.

FIG. 12 is a graph showing broadband PL of 590-nm QDs after propagation through a sample comprising bovine hemoglobin in a biological buffer. As seen therein, the broadband PL of 590-nm QDs is significantly altered upon propagation through the sample. Depth and concentration information can be extracted by analysis of these spectra.

The photoluminescent spectrum of the materials utilized in the devices, structures and methodologies disclosed herein may be modified or tailored as desired through appropriate selection of the luminescent materials and/or the dimensions of these materials. For example, FIG. 10 is a graph of the photoluminescence arising from different sizes and compositions of CuInZnSeS quantum dots that show many different emission wavelengths of these quantum dots that span the spectral range from 400-1200 nm. By mixing different combinations of quantum dots, the shape of the spectrum may be readily modified and tailored to the ideal spectrum. The shape of the spectrum, including the number of peaks, number of troughs, slope of the spectrum, and other signatures, may be tailored based on the size and composition of the quantum dots chosen. The QDs mixtures have an emission quantum yield of greater than 50%. It will be appreciated that this approach may be utilized to achieve a spectral output that is most conducive to the specific application.

Various luminescent materials may be utilized in the devices, structures and methodologies disclosed herein. As previously noted, one class of such materials are the colloidal semiconductor nanocrystals commonly known as quantum dots (QDs). These materials are advantageous in that they provide various size-tunable optical properties (including size tunable photoluminescence), and may be inexpensively processed from liquids. QDs are very effective at absorbing a broad spectrum of light and then converting that energy into emitted light of a single color that is determined by their size. Optical properties (such as, for example, absorption and emission spectra, PL lifetimes and Stokes shift) may be programmed into these materials by tailoring the manufacturing conditions to realize different sizes, shapes, compositions, and/or heterostructuring.

Focused efforts were made to build a prototype of the broadband light source using an alternative (simplified) approach (see FIG. 11). In particular, visible QDs were incorporated in a small (1×1×0.1 cm) piece of polymer—a miniature version of a luminescent solar concentrator (LSC). An optical fiber was also incorporated into the same polymer, and all the sides of the LSC, except one, were covered with reflective paint to improve light coupling to the optical fiber. The QDs were excited by a small blue LED (available commercially as ChanZon 10DGL-DZ-3W-BL). The PL concentrated in the LSC was coupled into the optical fiber and delivered to its other end, connected to a Thorlabs SMA fiber adapter. The output of the device was measured using a fiber-coupled spectrometer at a short (1.5 ms) integration time. Bright emission out of the fiber was easily observed by eye, both when the LSC was excited by a regular blue flashlight (left) as well as when using the blue LED (right). This simple prototype illustrates a unique, tunable light source. By combining several small LSCs with individually-colored QDs and allowing independent control over the excitation power for each of them, a miniature (yet highly flexible) broadband light source may be produced. For example, the output spectrum may be easily modified to compensate for the drop of the sensitivity of Si detectors around 1000-1100 nm.

PL of a single-sized QDs with ~590-nm peak was used to confirm that even PL spectrum of a single distinct type of $CuInSe_xS_{2-x}/ZnS$ QDs is broad enough to see signatures of some of the biological species. Specifically, (see FIG. 12), distinct absorption peaks of bovine hemoglobin were found to affect spectral shape and intensity of the QDs PL as it propagates through the sample (liquid solution of the bovine hemoglobin in biologically-relevant buffer, PBS). The arrow in FIG. 12 depicts increasing concentration of the bovine hemoglobin, which is a good proxy for increasing thickness of tissues.

Figure 13:
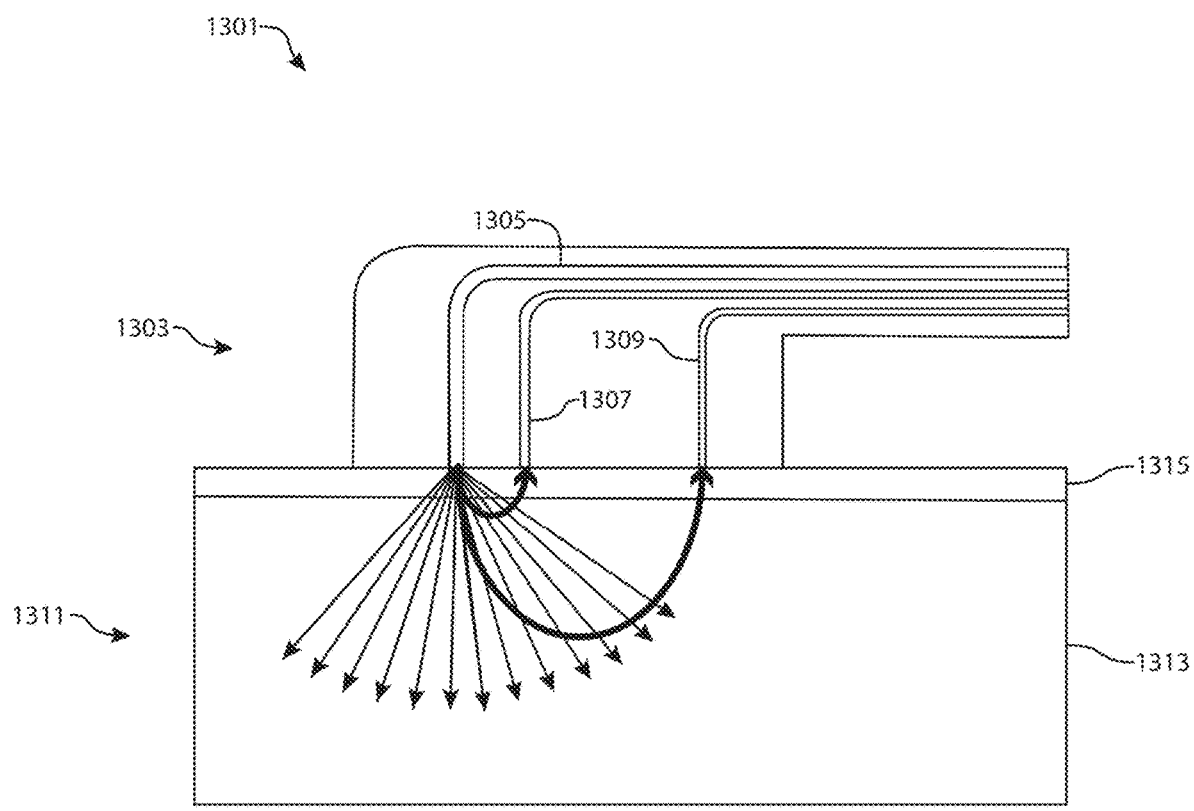
FIG. 13 is an illustration of a diffuse optical spectroscopic imaging device in accordance with the teachings herein.

FIG. 13 is an illustration of a particular, non-limiting embodiment of an optical spectroscopic imaging device in accordance with the teachings herein. Diffuse Optical Spectroscopic Imaging (DOSI) is a non-invasive optical diagnostic technique that can quantify the absorption and scattering coefficients of tissues up to several centimeters deep. By measuring these optical properties, quantifiable and qualitative information about the target tissue can be ascertained. DOSI is based on basic spectroscopic theories, and more specifically, on optical spectroscopy in the region of the electromagnetic spectrum extending from approximately 800 nm to 2500 nm near-infrared (NIR). DOSI works by interrogating the target tissue with NIR light, and detecting the remitted photons. The remission is then analyzed via a set of mathematical photon transport models based on the Beer-Lambert Law modified to predict multiple photon scattering and diffusion in living tissues. From this, various useful information may be derived such as, for example, tissue oximetry that may be utilized to diagnose conditions such as melanoma.

Figure 14:
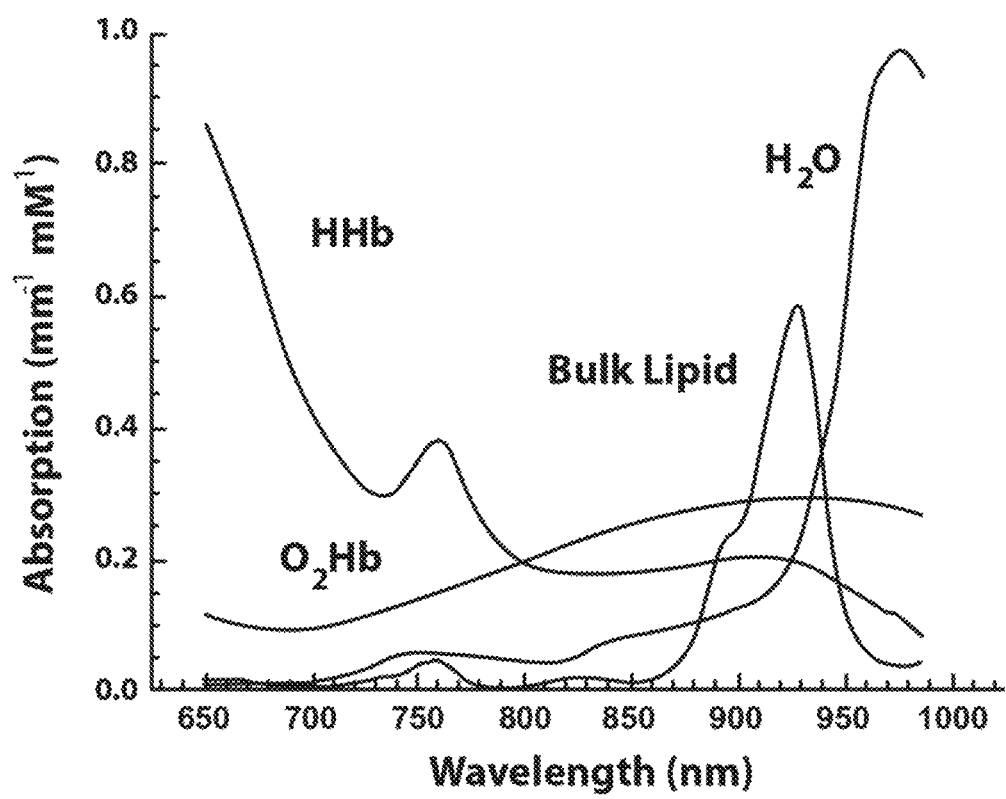
FIG. 14 is an example of an absorption spectra of various chromophores at different wavelengths (including NIR) which may be obtained with the device depicted in FIG. 13.

As can be seen in FIG. 14, a typical DOSI instrument consists of a probe 1101 equipped with a tunable NIR laser light source 1103 and various photon detectors 1105, 1106 placed at differing distances away from the light source 1103. The light source 1103 may be of the type disclosed herein. When laser light from the light source 1103 enters the region of interest, it begins to scatter and diffuse in a "banana" shaped fashion throughout the tissue 1107. This "banana" shaped light diffusion path is the reason why detectors closest to the source are able to analyze superficial portions of the tissue (such as subcutaneous tissue 1109), while the furthest detectors are capable of a deeper interrogation (such as skeletal muscle 1111). There is a limit to how far away the detectors can be.

DOSI operates on the principal that every chromophore in the target tissue absorbs the most light at their own unique and specific wavelength. This can be seen in FIG. 14, which is an example of absorption spectra of various chromophores at different wavelengths (including NIR) which may be obtained with the device depicted in FIG. 13. For example, water absorption of NIR light is highest around the 980 nm range. Notably, oxygenated and de-oxygenated hemoglobin have dramatically different absorption profiles, and are thus relatively easy to differentiate from one another. By measuring the tissue-photon interaction during DOSI studies, chromophore content and composition can be individually separated and analyzed to determine, for example, differences between benign lesions and malignant melanoma.

5. Additional Comments

Various modifications, substitutions, combinations, and ranges of parameters may be made or utilized in the compositions, devices and methodologies described herein.

For example, in some embodiments, the photoluminescence of the luminescent material may have a maximum intensity at wavelengths in the range of 400 nm to 2000 nm, more preferably in the range of 550 nm to 1700 nm, and most preferably in the range of 550 nm to 750 nm. In some embodiments, the fluorophores may emit a spectrum of light having full-width at half maximum intensity that is greater than 1 nm, greater than 20 nm, greater than 30 nm, greater than 40 nm, greater than 100 nm, or greater than 200 nm. In other embodiments, the photoluminescence of the luminescent material may have a maximum intensity at wavelengths greater than 550 nm.

In some embodiments, the photoluminescence of the luminescent material may be characterized by a quantum yield of at least 30%, at least 50%, at least 70%, or at least 80%.

Various optical elements may be utilized in the optical paths of the devices and methodologies described herein. For example, in some embodiments, a spectrum selecting optical element may be placed in the optical path between the irradiated article and the incident sunlight. Such an optical element may include, for example, one or more elements selected from the group consisting of light filters, quantum dot films and colored glasses. A spectrum selecting optical element of this type may allow only a given portion of the spectrum to pass.

QDs and fluorophores of various composition may be utilized in the systems and methodologies disclosed herein. Some of these compositions have been noted above. In some embodiments of the systems and methodologies described herein, QDs and fluorophores having compositions selected from the group consisting of $CuInS_2$, $CuInSe_2$, $AgInS_2$, $AgInSe_2$, ZnS, ZnSe, CuInZnSeS, $CuGaS_2$, and alloys of the foregoing, may be utilized. However, in many embodiments of the systems and methodologies disclosed herein, the use of QDs and fluorophores having the composition $CuInSe_xS_{2-x}/ZnS$ are preferred.

In some embodiments, two or more distinct types of quantum dots may be utilized in the systems, methodologies and compositions described herein. These quantum dots may be compositionally distinct. For example, the luminescent materials utilized herein may comprise a first type of quantum dot based on a first chemistry, and a second type of quantum dot based on a second chemistry which is distinct from the first chemistry. Thus, for example, the first type of quantum dot may comprise, for example, $CuInS_2$, while the second type of quantum dot may comprise $AgInSe_2$. Similarly, the luminescent materials described herein may comprise a first type of quantum dot based on a first set of dimensions (or distribution of dimensions) of the quantum dots, and a second type of quantum dot based on a second set of dimensions (or distribution of dimensions) of the quantum dots which is distinct from the first set of dimensions (or distribution of dimensions) of the quantum dots. Thus, for example, the first type of quantum dot may comprise generally spherical quantum dots having a first diameter (e.g., 10 nm), and the second type of quantum dot may comprise generally spherical quantum dots having a second diameter (e.g., 30 nm).

The devices, structures and methodologies disclosed herein have frequently been described herein in reference to their use in medical applications in general, and in diffuse optical spectroscopy in particular. However, one skilled in the art will appreciate that these devices, structures and methodologies may be employed in various other applications as well including, for example, general lighting applications.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

Moreover, it is specifically contemplated that the features described in the appended claims may be arranged in different combinations or sub-combinations without departing from the scope of the present disclosure. For example, it is contemplated that features set forth in two or more claims may be combined into a single claim without departing from the scope of the present disclosure, whether or not the resulting combination of features is explicitly disclosed elsewhere in the appended claims or disclosure.

What is claimed is:

1. An optical element, comprising:
   an optical fiber having a core comprising a solid medium; and
   a plurality of fluorophores disposed in said solid medium;
   wherein said plurality of fluorophores have a quantum yield greater than 50%, and wherein said plurality of fluorophores emit a spectrum of light having a maximum intensity at wavelengths within the range of 400 nm to 2000 nm; and
   wherein said plurality of fluorophores are quantum dots comprising a material selected from the group consisting of $CuInS_2$, $CuInSe_2$, $AgInS_2$, $AgInSe_2$, ZnS, ZnSe, and alloys of the foregoing.

2. The optical element of claim 1, wherein said plurality of fluorophores emit a spectrum of light having a maximum intensity at wavelengths greater than 550 nm.

3. The optical element of claim 1, wherein said optical element has an average transparency of greater than 50% at wavelengths within the range of 550 nm to 1700 nm.

4. The optical element of claim 1, wherein said plurality of fluorophores are quantum dots.

5. The optical element of claim 1, wherein said optical fiber further comprises a cladding, wherein said solid medium is polymer.

6. The optical element of claim 1, further comprising:
   at least one blue or UV LED optical element which is disposed at the end of, or along a portion of, said optical fiber and which is in optical communication therewith.

7. The optical element of claim 1, wherein said optical element is configured to be in optical communication with a spectrometer, wherein said spectrometer is configured to receive and analyze the spectrum of light emitted by the plurality of fluorophores.

8. The optical element of claim 1, wherein said optical element is configured to be in optical communication with a light source, wherein said plurality of fluorophores scatter incoming light from the light source by less than 5%.

9. The optical element of claim 1, wherein said plurality of fluorophores includes a first plurality of a first fluorophore and a second plurality of a second fluorophore, wherein said first and second fluorophores are distinct, and wherein said first plurality of said first fluorophore and said second plurality of said second fluorophore are homogeneously mixed within the solid medium.

10. The optical element of claim 1, wherein said optical element is configured to be in optical communication with a light source, wherein said plurality of fluorophores includes a set of fluorophores $F=F_1, \ldots, F_n$, wherein $n \geq 2$, wherein each fluorophore $F_i$, where $i \in [1, \ldots, n]$, has an emission spectrum characterized by a maximum intensity at wavelength $\lambda_i$, wherein $\lambda_1 > \ldots > \lambda_n$, and wherein said plurality of fluorophores are arranged within said optical fiber to form a gradient;
   wherein the gradient of said plurality of fluorophores is such that fluorophores $F=F_1, \ldots, F_n$ have maximum concentrations at respective distances from said light source of $d_1, \ldots, d_n$, wherein $d_1 < \ldots < d_n$.

11. The optical element of claim 1 wherein said optical element is configured to be in optical communication with a light source, wherein said plurality of fluorophores includes a set of fluorophores $F=F_1, \ldots, F_n$, wherein $n \geq 2$, wherein each fluorophore $F_i$, where $i \in [1, \ldots, n]$, has an emission spectrum characterized by a maximum intensity at wavelength $\lambda_i$, wherein $\lambda_1 > \ldots > \lambda n$, and wherein said plurality of fluorophores are arranged within media attached to the said optical fibers, and the said optical fibers are connected to the common output optical fiber.

12. The optical element of claim 1, wherein said optical element is configured to manipulate an output spectrum of light passing through said optical element such as to optimize signal-to-noise across the entire spectral range by matching an illumination intensity with the sensitivity profiles of a detection system.

13. The optical element of claim 1, wherein said optical element is configured to manipulate an output spectrum of light passing through said optical element such as to optimize signal-to-noise across the entire spectral range by matching the absorption profile of the tissues to the output spectrum of light passing through the optical element.

14. The optical element of claim 1, wherein said fluorophores have Stokes shifts of at least 50 nm.

15. The optical element of claim 1, wherein said fiber optic is segmented into a plurality of interchangeable segments.

16. The optical element of claim 1, wherein said fluorophores are configured to emit a spectrum of light having full-width at half maximum intensity of greater than 40 nm.

17. A spectral tissue sensing (STS) device, comprising:
an optical element, said optical element comprising
an optical fiber having a core comprising a solid medium; and
a plurality of fluorophores disposed in said solid medium;
wherein said plurality of fluorophores have a quantum yield greater than 50%, and wherein said plurality of fluorophores emit a spectrum of light having a maximum intensity at wavelengths within the range of 400 nm to 2000 nm; and
wherein said plurality of fluorophores are quantum dots comprising a material selected from the group consisting of $CuInS_2$, $CuInSe_2$, $AgInS_2$, $AgInSe_2$, $ZnS$, $ZnSe$, and alloys of the foregoing;
wherein said STS device further comprises:
a light source;
a visible spectrometer;
an infrared spectrometer;
an optical probe comprising an illumination fiber, a first detection fiber and a second detection fiber, wherein said illumination fiber comprises said optical element and is configured to be in optical communication with said light source, wherein said first detection fiber is configured to be in optical communication with said visible spectrometer, and wherein said second detection fiber is configured to be in optical communication with said infrared spectrometer.

18. The STS device of claim 17, wherein said light source is a broadband light source.

* * * * *